(12) United States Patent
Rankin et al.

(10) Patent No.: US 9,161,835 B2
(45) Date of Patent: Oct. 20, 2015

(54) NON-AXISYMMETRIC AORTIC VALVE DEVICES

(75) Inventors: J. Scott Rankin, Nashville, TN (US); Al Beavan, Kingsland, TX (US); William E. Cohn, Bellaire, TX (US)

(73) Assignee: Biostable Science & Engineering, Inc., Austin, TX (US)

( * ) Notice: Subject to any disclaimer, the term of this patent is extended or adjusted under 35 U.S.C. 154(b) by 0 days.

(21) Appl. No.: 13/430,642

(22) Filed: Mar. 26, 2012

(65) Prior Publication Data

US 2012/0239143 A1  Sep. 20, 2012

Related U.S. Application Data

(63) Continuation-in-part of application No. 13/250,720, filed on Sep. 30, 2011.

(60) Provisional application No. 61/388,575, filed on Sep. 30, 2010.

(51) Int. Cl.
A61F 2/24 (2006.01)

(52) U.S. Cl.
CPC ............. *A61F 2/2445* (2013.01); *A61F 2/2418* (2013.01); *A61F 2/2463* (2013.01); *A61F 2220/0075* (2013.01); *A61F 2230/0008* (2013.01); *A61F 2230/0013* (2013.01); *A61F 2230/0054* (2013.01); *A61F 2250/0087* (2013.01)

(58) Field of Classification Search
CPC .... A61F 2/2412; A61F 2/2418; A61F 2/2445

USPC ................. 623/1.24, 1.26, 2.1–2.19
See application file for complete search history.

(56) References Cited

U.S. PATENT DOCUMENTS

| | | |
|---|---|---|
| 3,548,418 A | 12/1970 | Angell et al. |
| 3,714,671 A | 2/1973 | Edwards et al. |
| 3,739,402 A | 6/1973 | Cooley et al. |
| 4,035,849 A | 7/1977 | Angell et al. |
| 4,106,129 A | 8/1978 | Carpentier et al. |

(Continued)

FOREIGN PATENT DOCUMENTS

| | | |
|---|---|---|
| EP | 1258232 A2 | 11/2002 |
| GB | 1264472 | 2/1972 |

(Continued)

OTHER PUBLICATIONS

International Search Report, International Patnet Application No. PCT/US2011/054160, May 29, 2012.

(Continued)

*Primary Examiner* — Jason-Dennis Stewart
(74) *Attorney, Agent, or Firm* — Patterson Intellectual Property Law, P.C.; Hilary Dorr Lang; Ryan D. Levy

(57) ABSTRACT

The present disclosure provides aortic valve prosthetic devices that are constructed in a non-axisymmetric shape, or are expandable to a non-axisymmetric shape for improved results in the repair of defective aortic valves. The devices can be surgically implanted, or they can be implanted percutaneously through an insertion catheter. The expandable devices can be self-expanding or expanded by an inflatable balloon to a non-axisymmetric cross-section geometry.

23 Claims, 9 Drawing Sheets

(56) References Cited

U.S. PATENT DOCUMENTS

| | | |
|---|---|---|
| 4,451,936 A | 6/1984 | Carpentier et al. |
| 4,491,986 A | 1/1985 | Gabbay |
| 4,501,030 A | 2/1985 | Lane |
| 5,258,021 A | 11/1993 | Duran |
| 5,607,471 A | 3/1997 | Seguin et al. |
| 5,728,152 A | 3/1998 | Mirsch et al. |
| 5,910,170 A | 6/1999 | Reimink et al. |
| 6,231,602 B1 | 5/2001 | Carpentier et al. |
| 6,258,122 B1 | 7/2001 | Tweeden et al. |
| 6,539,984 B2 | 4/2003 | Lam |
| 6,544,285 B1 | 4/2003 | Thubrikar et al. |
| 6,610,088 B1 | 8/2003 | Gabbay |
| 6,613,086 B1 | 9/2003 | Moe et al. |
| 6,695,879 B2 | 2/2004 | Bell |
| 6,733,525 B2 | 5/2004 | Yang et al. |
| 6,767,362 B2 | 7/2004 | Schreck |
| 7,294,148 B2 | 11/2007 | McCarthy |
| 7,320,704 B2 | 1/2008 | Lashinski et al. |
| 7,682,389 B2 | 3/2010 | Beith |
| 7,815,677 B2 | 10/2010 | Jaffe et al. |
| 7,871,435 B2 | 1/2011 | Carpentier et al. |
| 8,034,102 B2 | 10/2011 | Bulman-Fleming et al. |
| 8,163,011 B2 | 4/2012 | Rankin |
| 8,236,050 B2 | 8/2012 | Bolling et al. |
| 8,425,594 B2 | 4/2013 | Rankin |
| 2003/0093147 A1 | 5/2003 | Ogle et al. |
| 2004/0006384 A1 | 1/2004 | McCarthy |
| 2005/0065597 A1 | 3/2005 | Lansec |
| 2005/0149181 A1 | 7/2005 | Eberhardt |
| 2005/0228494 A1 | 10/2005 | Marquez |
| 2006/0020327 A1* | 1/2006 | Lashinski et al. ............ 623/1.25 |
| 2006/0293745 A1* | 12/2006 | Carpentier et al. .......... 623/2.19 |
| 2007/0027528 A1* | 2/2007 | Agnew .......................... 623/1.24 |
| 2008/0294248 A1 | 11/2008 | Yang et al. |
| 2009/0054973 A1 | 2/2009 | Johnson |
| 2009/0177271 A1 | 7/2009 | Fabiani |
| 2009/0192591 A1* | 7/2009 | Ryan et al. ................... 623/1.26 |
| 2009/0281618 A1 | 11/2009 | Hill et al. |
| 2010/0094411 A1 | 4/2010 | Tuval et al. |
| 2010/0217371 A1* | 8/2010 | Noone et al. |
| 2010/0256750 A1* | 10/2010 | Forster et al. ................ 623/2.11 |
| 2010/0268324 A1 | 10/2010 | Eberhardt et al. |
| 2010/0268332 A1* | 10/2010 | Tuval et al. |
| 2011/0282440 A1 | 11/2011 | Cao et al. |
| 2013/0023980 A1 | 1/2013 | Drasler |

FOREIGN PATENT DOCUMENTS

| | | |
|---|---|---|
| WO | WO 97/16135 A1 | 5/1997 |
| WO | WO 00/62715 A1 | 10/2000 |
| WO | WO 03/041617 A1 | 5/2003 |
| WO | WO 2007/024755 A1 | 3/2007 |
| WO | WO 2007/046000 A1 | 4/2007 |
| WO | WO 2008/045651 A2 | 4/2008 |
| WO | WO 2008/133852 A1 | 6/2008 |

OTHER PUBLICATIONS

International Search Report, International Patnet Application No. PCT/US2011/054359, May 31, 2012.

Co-Pending U.S. Appl. No. 13/249,621, filed Sep. 30, 2011.

Co-Pending U.S. Appl. No. 13/250,720, filed Sep. 30, 2011.

"Ellipse," Pail's Online Math Notes, Paul Dawkins, pp. 1-3, accessed Sep. 26, 2013.

"A General Kind of Circles—Ellipses," pp. 1-3, accessed Sep. 26, 2013.

Itoh et al. "Mitral annular hinge motion contribution to changes in mitral septal-lateral dimension and annular area" J. Thorac Cariovasc Surg 2009;138:1090.

Jensen et al. "Saddle-shaped mitral valve annuloplasty rings improve leaflet coaptation geometry" J. Thorac Cardiovasc Surg 2011;142:697.

Rankin et al. "A refined hemispheric model of normal human aortic valve and root geometry" J. Thorac Cardiovasc Surg 2013;146:103.

Crooke et al. "Design Characteristics of a Three-Dimensional Geometric Aortic Valve Annuloplasty Ring" Innovations 2013;8:364.

Office Action mailed on Jul. 6, 2015 in U.S. Appl. No. 13/250,720.

* cited by examiner

NON-AXISYMMETRIC AORTIC VALVE DEVICES

CROSS-REFERENCE TO RELATED APPLICATION

This application is a continuation-in-part of U.S. patent application Ser. No. 13/250,720, filed on Sep. 30, 2011, which claims the benefit of U.S. Provisional Patent Application Ser. No. 61/388,575, filed on Sep. 30, 2010, both of which are incorporated herein by reference in their entirety.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE ART

The mammalian heart is essentially a pump that functions as a chemo-mechanical energy transducer. The chemical energy of metabolic substrates and oxygen is converted into the mechanical energy of blood pressure and flow by myocardial sarcomeres during cardiac contraction. The pump is periodic at a frequency of 1-2 Hz, with the contraction/ejection phase called systole and the relaxation/filling phase termed diastole.

The human heart is the center of the cardiovascular system, the system having two parallel circulations consisting of the pulmonary circulation and the systemic circulation. The pulmonary circulation receives blood from the venae cavae into the right atrium and right ventricle, and then pumps the cardiac output into the pulmonary arteries and through the lungs. The systemic circulation receives blood from the pulmonary veins, pumps the cardiac output through the left atrium and left ventricle to the aorta, systemic arteries, capillaries, and veins, and finally transmits blood back to the venae cavae. The mitral valve is positioned between the upper chamber, the left atrium, and the pumping chamber, the left ventricle. The left atrium acts in a capacitor function receiving blood from the lungs via the pulmonary veins throughout the cardiac cycle. The left ventricle fills during diastole by receiving blood from the left atrium as the mitral valve opens, and then during systole, the mitral valve closes and permits forward ejection of the blood from the left ventricle into the ascending aorta. The aortic valve is located between the left ventricle and aorta, and functions under normal conditions to allow unimpeded blood flow out of the ventricle and into the aorta during systole. During diastole, the aortic valve closes and prevents regurgitation backward into the left ventricle.

Surgical reconstruction of a patient's native valve is becoming standard for mitral valve disease. Whether considering mitral valve prolapse, pure annular dilatation, ischemic mitral regurgitation, or mitral endocarditis, repair is now routine, highly successful, and associated with low late failure rates. Even in rheumatic mitral disease, many surgeons are embarking on programs of aggressive repair, adding to ring annuloplasty the techniques of posterior leaflet augmentation with gluteraldehyde-fixed autologous pericardium, resection of the stenotic submitral apparatus with insertion of artificial GORTEX™ chords, leaflet decalcification, etc. The current goal is to achieve close to a 100% repair rate of mitral valve disorders and to markedly diminish prosthetic valve replacement. The advantages of repair versus replacement in this setting are well documented. The operative mortality rate (normalized for other factors) is lower, anticoagulation is not required in sinus rhythm, valve-related complications are less than with prosthetic valves, durability is excellent because the patient's own tissues do not degenerate, and late endocarditis is reduced because less foreign material is present. As such, these concepts for mitral valve disease are rapidly becoming standard-of-care in the field of cardiac surgery.

The aortic valve of a human heart can also become diseased, with aortic valve insufficiency occurring from a number of causes. A common cause is annular dilatation, with the sinuses of the Valsalva migrating outward and the inter-commissural distances expanding. Geometrically, this derangement not only increases the annular circumference, but also reduces the surface area of cusp coaptation. The coaptation angle of the cusps is changed essentially from being parallel and meeting at an acute angle to pointing at each other, wherein the cusps comprise a more obtuse arrangement. Eventually, a central gap of coaptation occurs and increasing aortic insufficiency begets more annular dilatation which begets more aortic insufficiency and the leak progressively increases.

Repair of a diseased aortic valve has not been met with the same success as experienced in reconstructing a diseased mitral valve. For about 10 to 15 years, the "commissural annuloplasty" technique has been used, but it can only be applied to mild-to-moderate secondary aortic insufficiency, usually in patients undergoing primary coronary bypass or mitral valve procedures. Commissural annuloplasty not only decreases annular circumference, but also tends to move the sinuses centrally, thus normalizing geometry and coaptation angles of the cusps. There is a limit, however, to the geometric abnormality that commissural annuloplasty can normalize, and because the entire annulus is not fixed by this procedure, the potential for further dilatation and recurrent aortic insufficiency exists.

As such, devices and methods have been proposed including, for example, U.S. Pat. No. 4,451,936 ("the '936 patent"), which teaches a supra-annular aortic valve. According to the '936 patent, the invention is applicable to mechanical heart valves and leaflet-type heart valves, and does not project into the aortic valve. In U.S. Pat. No. 5,258,021 ("the '021 patent"), an annuloplasty ring is described for insertion inside the aorta in the supra-annular region above the aortic valve annulus. The disclosed device appears circular from above and has three substantially sinusoidal shaped struts. In U.S. Patent Application Publication No. 2005/0228494 ("the '494 patent application"), a heart valve frame is described which can separate into a plurality of individual cusps after implantation. Additionally, the invention of the '494 patent application is preferably used with synthetic leaflets.

U.S. Pat. No. 6,231,602 ("the '602 patent") describes an annuloplasty ring sutured to the tissue above the aortic valve annulus and also an infra-annular ring which can be sutured to the dense tissue immediately below the commissural-arterial wall intersection. Moreover, the infra-annular ring does not alter or even influence leaflet geometry in an organized manner, but instead constricts the infra-annular aorta to move the inferior aspects of the leaflets centrally rather than restore proper leaflet coaptation. Furthermore, as the ring of the '602 patent is apparently based on previous studies of the mitral valve, the '602 neglects the complexities of the 3-dimensional geometry of the aortic valve and ineffectively constricts either the supra-valvular or infra-valvular area. Also, the '602 patent describes the ring as only following the rough shape of the aortic tissue either above or below the valve annulus and neither provides an explanation of the proper sizing of the ring nor describes how the ring will be implanted within the patient.

The supra- or infra-annular rings and artificial valves of the prior art processes are generally circular (or axisymmetric) in shape. An axisymmetric shape is one that can be superimposed on itself more than twice in a 360 degree rotation. A circle and an equilateral triangle are examples of axisymmetric shapes. Unfortunately, such axisymmetric devices are generally not effective for the long term improvement of the aortic valve, and additionally, may require quite complicated surgical procedures.

What is desired, therefore, are improved devices for aortic valve repair or replacement. Also desired are processes for inserting and mounting such devices.

BRIEF SUMMARY OF THE INVENTION

The present disclosure arises from the surprising discovery that aortic valve devices, implants and prostheses provide the correct orientation, placement and coaptation angles of valve leaflet structures (either the natural or synthetic valve leaflets) when the device is configured to have a non-axisymmetric shape in a plane perpendicular to the direction of blood flow through the aortic valve, or in certain embodiments, when the device is configured to adopt a non-axisymmetric shape in a plane perpendicular to the direction of blood flow through the aortic valve once it is inserted into the aortic valve region. As defined herein, the term "non-axisymmetric shape" is a geometrical shape that is not superimposable on itself more than twice during a 360 degree rotation. An example of a non-axisymmetric shape is an ellipse. Thus, the present disclosure provides non-axisymmetric devices, implants and prostheses. As defined herein, the term "non-axisymmetric devices, implants and prostheses" is defined as devices, implants and prostheses that have a non-axisymmetric shape, or are non-axisymmetrically constructed. As defined herein, the term "non-axisymmetrically constructed" devices, implants or prostheses are devices, implants or prostheses that initially may have an axisymmetric shape, but that are specifically designed to adopt a non-axisymmetric shape once placed into the aortic valve region through the use of two or more different materials, two or more thicknesses of material, or a combination thereof. An example of a non-axisymmetrically constructed device, implant or prosthesis is a generally circular device, implant or prosthesis wherein at least one portion of the circular device, implant or prosthesis is made from a different material, a different thickness of material, or a combination thereof, than the remainder of the circular device, implant or prosthesis. The non-axisymmetric devices, implants and prostheses described herein are specifically designed to avoid or reduce pressure on the atrioventricular node (AV node).

Furthermore, when the natural valve is to be repaired, instead of replaced, the device is configured to have commissure-support regions that flare outward (toward the aortic wall) from a vertical plane passing through the interior area of the device or implant. Certain devices include a base that is a rigid or expandable ring structure to which other features are attached. When such a base is present, it is in the form of a non-axisymmetric shape in the plane perpendicular to the vessel walls, or in devices that do not include a ring structure, the general cross-sectional geometry of the devices has non-axisymmetric cross-sectional geometry in that plane. The non-axisymmetric structure is shown herein to provide improved function and thus improved outcome for the recipient.

In particular embodiments, the non-axisymmetric shape is an ellipse. Generally, depending upon the specific geometry of the aortic valve of the patient, the ratio of the major axis of the ellipse to the minor axis of the ellipse is greater than 1, in certain aspects between about 1.1 and 1.8, including ratios of about 1.1, about 1.2, about 1.3, about 1.4, about 1.5, about 1.6, about 1.7, and about 1.8. The ellipse defined by the intra-annular mounting frame can also be expressed as the ratio of the minor axis to the major axis. As such, the presently described intra-annular mounting frame can have a ratio of the minor axis to the major axis of less than 1, in certain aspects about 0.9, about 0.85, about 0.80, about 0.75, about 0.70, about 0.65, about 0.60, or about 0.55 or so. In various embodiments the length of the major axis of the ellipse is between about 10 millimeters and about 35 millimeters, between about 15 millimeters and about 30 millimeters, between about 20 millimeters and about 25 millimeters, between about 10 millimeters and about 30 millimeters, between about 10 millimeters and about 25 millimeters, between about 10 millimeters and about 20 millimeters, between about 10 millimeters and about 15 millimeters, between about 15 millimeters and about 35 millimeters, between about 20 millimeters and about 35 millimeters, between about 25 millimeters and about 35 millimeters, or between about 30 millimeters and about 35 millimeters, including lengths of about 10 millimeters, about 11 millimeters, about 12 millimeters, about 13 millimeters, about 14 millimeters, about 15 millimeters, about 16 millimeters, about 17 millimeters, about 18 millimeters, about 19 millimeters, about 20 millimeters, about 21 millimeters, about 22 millimeters, about 23 millimeters, about 24 millimeters, about 25 millimeters, about 26 millimeters, about 27 millimeters, about 28 millimeters, about 29 millimeters, about 30 millimeters, about 31 millimeters, about 32 millimeters, about 33 millimeters, about 34 millimeters, and about 35 millimeters. The length of the minor axis of the ellipse can also vary, for example between about 8 millimeters and about 25 millimeters, between about 10 millimeters and about 21 millimeters, between about 14 millimeters and about 18 millimeters, between about 8 millimeters and about 20 millimeters, between about 8 millimeters and about 15 millimeters, between about 10 millimeters and about 25 millimeters, between about 15 millimeters and about 25 millimeters, or between about 20 millimeters and about 25 millimeters, including lengths of about 8 millimeters, about 9 millimeters, about 10 millimeters, about 11 millimeters, about 12 millimeters, about 13 millimeters, about 14 millimeters, about 15 millimeters, about 16 millimeters, about 17 millimeters, about 18 millimeters, about 19 millimeters, about 20 millimeters, about 21 millimeters, about 22 millimeters, about 23 millimeters, about 24 millimeters, and about 25 millimeters.

In certain aspects wherein the existing aortic valve is to be repaired, instead of replaced, and generally depending upon the specific geometry of the aortic valve of the patient, the edge regions of the described aortic repair devices flare outward from a vertical plane passing through the interior area of the device, implant or prosthesis at an angle of about 1 degree, about 2 degrees, about 3 degrees, about 4 degrees, about 5 degrees, about 6 degrees, about 7 degrees, about 8 degrees, about 9 degrees, about 10 degrees, about 11 degrees, about 12 degrees, about 13 degrees, about 14 degrees, about 15 degrees, about 16 degrees, about 17 degrees, about 18 degrees, about 19 degrees, about 20 degrees, about 21 degrees, about 22 degrees, about 23 degrees, about 24 degrees, about 25 degrees, about 26 degrees, about 27 degrees, about 28 degrees, about 29 degrees, or about 30 degrees or more.

The disclosed devices can be either of the mechanical, polymer, biopolymer, or bileaflet carbon types of aortic valve implants or prostheses, or any combination thereof. The devices can be constructed of a rigid metal, pyrolytic carbon, or polymer material, for example, or of a metal or polymer cage structure. For example, different portions of the non-axisymmetrically constructed device, implant or prosthesis can be made from different alloys, such as different shape-memory alloys. The most common types of shape-memory alloys are the copper-zinc-aluminum-nickel, copper-aluminum-nickel, and nickel-titanium (NiTi; nitinol) alloys, but shape-memory alloys can also be created by alloying zinc, copper, gold and iron. Additionally the non-axisymmetrically constructed device, implant or prosthesis can be made from two different materials, including, but not limited to, a shape memory alloy and a cobalt chromium alloy, a shape memory or cobalt chromium alloy and a polymer or plastic, two or more different polymers, or two or more materials with different elastic coefficients. Certain devices are designed to be surgically implanted and sutured into the valve and can include a non-axisymmetric (e.g., elliptical) annular ring support structure. In certain embodiments the implant or prostheses is constructed of biological materials including biopolymers such as collagen, for example, and can further include seeded cells or signaling molecules in the structure.

In certain embodiments the present disclosure provides a non-axisymmetric sewing ring for attachment of a heart valve to the aortic wall of a host, comprising a biopolymer cloth and a biopolymer rope in a non-axisymmetric shape, or shaped in an ellipse, wherein the biopolymer cloth is wrapped around and stitched to the biopolymer rope.

In additional embodiments the present disclosure provides a non-axisymmetric prosthetic heart valve assembly comprising a fixation ring having an inner periphery defining an opening through the fixation ring and an outer periphery and adapted to be affixed to the natural annulus of a patient, a mounting ring having an inner peripheral surface defining an opening through the mounting ring, the mounting ring being coupled to the fixation ring with the openings being in registry whereby a prosthetic valve can be received in the opening of the mounting ring, a prosthetic valve receivable in the opening of the mounting ring, a retaining ring, means at least partially on said mounting ring for releasably attaching the retaining ring to the mounting ring so that the retaining ring can retain the prosthetic valve against moving in one direction out of the opening in the mounting ring when the prosthetic valve is received in the opening and the retaining ring can be removed without removing the prosthetic valve to permit replacement of the prosthetic valve with another prosthetic valve, and means for retaining the prosthetic valve against moving in another direction out of the opening in the mounting ring, wherein the fixation ring, the mounting ring and the retaining ring are non-axisymmetric in cross-sectional shape in a plane perpendicular to the direction of blood flow through the valve.

In other embodiments the present disclosure provides a non-axisymmetric tissue-type heart valve comprising a dimensionally stable, pre-aligned and pre-assembled tissue leaflet subassembly including a plurality of leaflets, wherein each leaflet includes a cusp edge opposite from a coapting edge and two leaflet tabs extending from the junctions between the cusp and coapting edges in generally opposite directions, the pre-alignment of the leaflets in the subassembly creating a plurality of pairs of mating leaflet tabs extending outward from the subassembly, one pair of mating leaflet tabs per adjacent pair of leaflets, a generally non-axisymmetric wireform having a bottom surface dimensioned to receive the pre-aligned tissue leaflet subassembly in fixed, mating engagement, the wireform having lower cusps interrupted by upwardly extending commissures, the cusp edges of the leaflets in the pre-assembled tissue leaflet subassembly being attached along the cusps of the wireform to form a leaflet/wireform subassembly, and a generally non-axisymmetric support stent having an upper surface dimensioned to seat and fix in mating engagement with the leaflet/wireform subassembly, the support stent having upwardly extending flexible commissure posts to which the pairs of mating leaflet tabs attach.

In additional embodiments the present disclosure provides a non-axisymmetric annuloplasty prosthesis for use in restoring the normal circumference of the dilated annulus and sinuses of a natural arterial heart valve having leaflets having a plurality of commissures, the non-axisymmetric prosthesis comprising an upper edge having a plurality of axially projecting legs, each of the legs corresponding to the location of a commissure of the valve and being sequentially interconnected by arcuate circumferential or perimeter segments of the upper edge, the upper edge thus defining a series of peaks and valleys, a lower edge disposed below and substantially adjacent to the upper edge and shaped to conform to the peaks and valleys of upper edge, the lower edge defining a series of peaks and valleys that is less pronounced than that of the upper edge, and a flexible biocompatible material covering the prosthesis. In embodiments wherein the natural arterial heart valve is not able to be used, the non-axisymmetric annuloplasty prosthesis includes a non-axisymmetric valve including an annulus, leaflets, and commissure points, and in various embodiments can be a mechanical valve, a bileaflet carbon valve, a tissue valve made from a biological material, such as an animal or human valve or tissue, or a synthetic valve, for example made from a polymer.

In further embodiments the present disclosure provides a non-axisymmetric prosthetic heart valve comprising a tri-composite, full root, stentless valve, that is devoid of coronary ostia, and that has been made by suturing together three pieces of animal tissue that each includes a heart valve leaflet to form a non-axisymmetric structure having an external surface, an inner surface, an posterior end, an anterior end, and in which the three leaflets have cusps and edges, with the adjacent edges of the valve leaflets meeting to form commissures, wherein the pieces have been treated by photochemical fixation prior to suturing.

In certain embodiments, the devices can constructed of a compressible and expandable material effective to be compressible into a percutaneous delivery system and expandable to a non-axisymmetric geometry when released. Such devices can be constructed of wire loops, helices or other open mesh structures to provide compressibility and expandability. The devices typically include a non-axisymmetric ring structure. In certain embodiments the devices are expanded by inflating a balloon (for example a nylon elliptical-shaped balloon) when the device is in the correct position, or the devices can be self-expanding. In certain embodiments a self-expanding device is composed of nitinol, a nickel-titanium alloy present in approximately equal amounts.

In other embodiments the present disclosure provides a non-axisymmetric valve prosthesis for implantation in a body channel, the non-axisymmetric valve prosthesis comprising a collapsible elastic valve that is mounted on an elastic stent, the elastic valve having a plurality of commissural points, wherein the stent comprises a non-axisymmetric support means that is radially collapsible for introduction within the body channel and that has a plurality of circumferentially-expandable sections such that the non-axisymmetric support means is radially expandable for being secured within the body channel, and a plurality of commissural supports projecting from one side of the non-axisymmetric support means in a direction generally parallel to the longitudinal axis thereof for supporting the commissural points of the collapsible valve, at least one circumferentially-expandable section of the non-axisymmetric support means lying between each of the commissural supports, such that the collapsible valve may be collapsed and expanded together with the non-axisymmetric support means for implantation in the body channel by means of a technique of catheterization. In yet other embodiments the present disclosure provides a non-axisymmetric valve prosthesis for implantation in a body channel having an inner wall, the prosthesis comprising a radially collapsible and expandable stent, the stent including a non-axisymmetric support means having a surface; and a collapsible and expandable valve having commissural points, the valve mounted to the stent at the commissural points, wherein the stent and valve are configured to be implanted in the body by way of catheterization. The present disclosure also provides a non-axisymmetric valve prosthesis for implantation in a body, comprising an elastic stent comprising a non-axisymmetric support having circumferentially expandable sections comprised of a series of loops with commissural supports therebetween and integral therewith, and an elastic valve, commissural points of which are mounted on a respective one of the commissural supports, wherein the non-axisymmetric support is radially collapsible for implantation in the body via a catheter.

In additional embodiments the present disclosure provides a non-axisymmetric prosthetic valve assembly for use in replacing a deficient native valve, the valve assembly comprising a non-axisymmetric valve having a plurality of resilient leaflets, a valve support comprising a non-axisymmetric central band comprising a plurality of expandable cells, the valve support configured to be collapsible for transluminal delivery and expandable to contact the anatomical annulus of the native valve when the assembly is positioned in situ, the valve support supporting the base and the commissure points of the valve, and an anchor for engaging the lumen wall when expanded in place for preventing substantial migration of the valve assembly after deployment, wherein the anchor is itself configured to be expandable.

The present disclosure further provides a non-axisymmetric intra-annular mounting frame for an aortic valve comprising a plurality of curvatures having ends, a plurality of points interconnecting the ends of each of the curvatures to form an interior area, and a plurality of posts extending upward from each of the points, wherein the points, the ends of the curvatures, and the posts define edge regions that flare outward from the interior area of the intra-annular mounting frame, and wherein the intra-annular mounting frame has a non-axisymmetric shape, or an elliptical shape having a major axis and a minor axis, wherein the major axis is greater in length than the minor axis. In certain embodiments the intra-annular mounting frame comprises three curvatures, three points, and three posts. An angle is defined between each of the posts in the intra-annular mounting frame. In some embodiments, generally depending upon the specific geometry of the aortic valve of the patient, the angle between each of the posts are equal (symmetrical), in other embodiments the angle between each of the posts are different (asymmetrical), while in yet other embodiments two of the angles between the posts are equivalent while the third angle is different from the other two (asymmetrical). In further embodiments the non-axisymmetric intra-annular mounting frame comprises two curvatures, two points, and two posts. Such embodiments are used in bicuspid aortic valve repair. In certain embodiments, generally depending upon the specific geometry of the bicuspid aortic valve of the patient, the angle between each of the posts are equal (symmetrical), while in other embodiments the angle between each of the posts are different (asymmetrical). In additional embodiments the posts are located along the curvatures defined by the major axis of the ellipse, the curvatures defined by the minor axis of the ellipse, or one post is located along the curvatures defined by the major axis of the ellipse while the other post is located along the curvatures defined by the minor axis of the ellipse.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" may mean a singular object or element, or it may mean a plurality, or one or more of such objects or elements. Additionally, in discussions of the elliptical shape of the devices, the terms "circumference" and "perimeter" are used interchangeably.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present disclosure arises at least in part from the discovery by the inventors that the annulus of the aortic valve is not circular, as generally believed in the art, but is actually non-axisymmetric in shape, and that the commissures of the aortic valve flare outward from the center of the valve. Therefore devices, implants and prostheses that are roughly non-axisymmetric in shape, or non-axisymmetric in construction, and that in certain embodiments have outwardly flaring commissures, will provide improved results in the repair of defective aortic valves. For simplicity the description below concerns elliptical aortic devices, implants and prostheses; however all manner of non-axisymmetric aortic devices, implants and prostheses are covered by the present disclosure.

Elliptical Valve Rings and Elliptical Mounting Frames

In certain embodiments, the present disclosure is directed to systems and methods in which an elliptical valve ring or elliptical mounting frame is implanted into the native valve of the patient. An exemplary embodiment of an elliptical aortic valve mounting frame is described in greater detail below.

Figure 1:
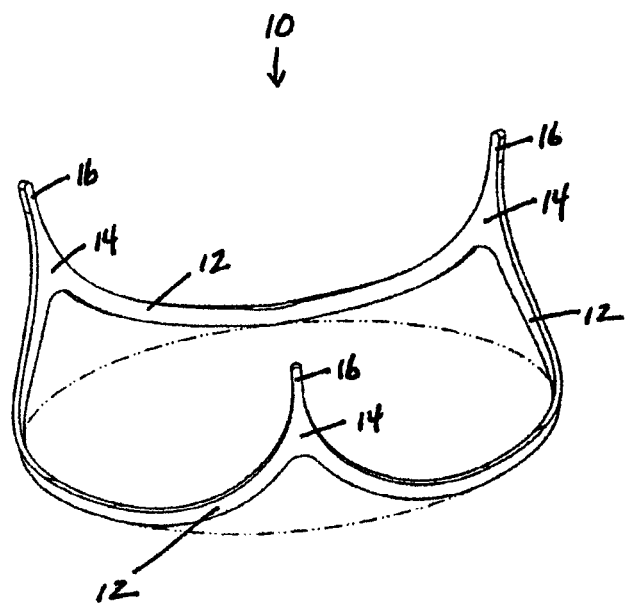
FIG. 1. Perspective view of one embodiment of an elliptical intra-annular mounting frame of the present disclosure.

Referring now to FIG. 1, a perspective view of an embodiment of an elliptical intra-annular mounting frame useful for aortic valve repair is shown and generally designated as numeral 10. Elliptical intra-annular mounting frame 10 is inserted into the aortic valve annulus and provides for the reconstruction of the native aortic valve.

Elliptical intra-annular mounting frame 10 includes a plurality of curvatures 12, interconnecting points 14, and posts 16. Generally, curvatures 12 conform to the annular cusp geometry with interconnecting points 14 and posts 16 conforming to the geometry of the sub-commissural region. Curvatures 12 curve in a plurality of planes of elliptical intra-annular mounting frame 10 to correspond to the three-dimensional geometry of the cusps of an aortic valve. For reference, the horizontal plane is defined as the plane on which elliptical intra-annular mounting frame 10 would rest with each curvature 12 contacting the plane. The vertical plane is defined as the plane which intersects the horizontal plane at a perpendicular angle and runs vertically through elliptical intra-annular mounting frame 10. Curvatures 12 may curve in both the horizontal and vertical planes, and/or may curve in one or more other planes. Generally curvatures 12 contact the aortic wall and provide support and alignment to the aortic valve cusps. Interconnecting points 14 and posts 16 provide support to the commissures of the aortic valve. Specifically, interconnecting points 14 and posts 16 are designed to closely fit the three-dimensional geometry between adjacent cusps and locate near the commissures thus providing support and assistance in the restoration of the proper coaptation of the cusps. Interconnecting points 14 continuously narrow to posts 16 and thus fit within the narrowing space between adjacent cusps that culminates in a commissure. As such, interconnecting points 14 and posts 16 provide support within this inter-cusp space to immediately below the commissures.

Figure 2:
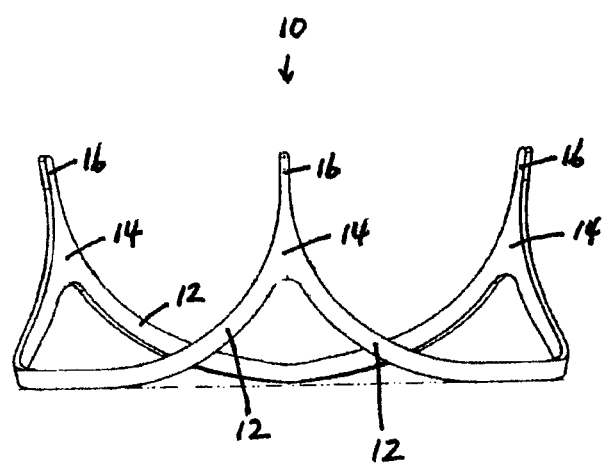
FIG. 2. Front elevational view of the embodiment of the elliptical intra-annular mounting frame shown in FIG. 1.

Referring now to FIG. 2, a front elevational view of elliptical intra-annular mounting frame 10 of FIG. 1 is shown. Once again elliptical intra-annular mounting frame 10 includes a plurality of curvatures 12, interconnecting points 14, and posts 16.

Figure 3:
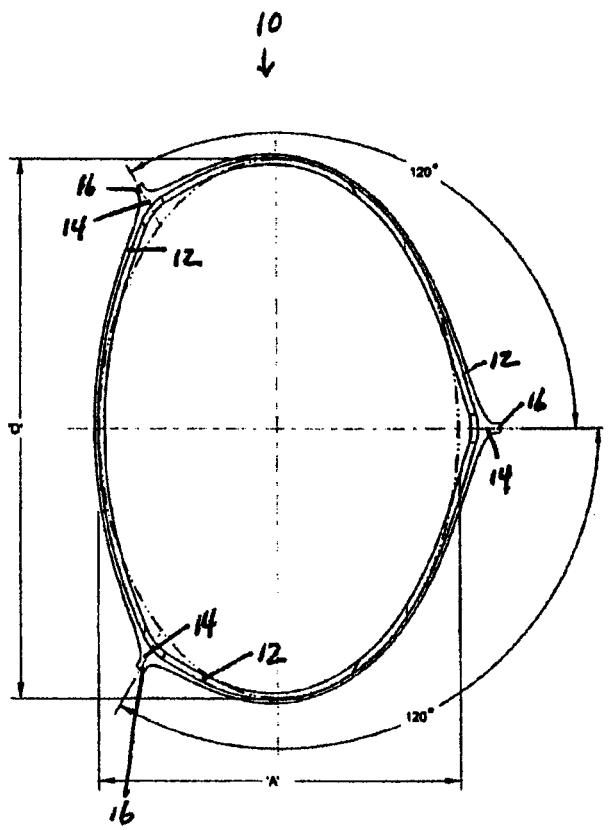
FIG. 3. Top view of the embodiment of the elliptical intra-annular mounting frame shown in FIG. 1.

Referring now to FIG. 3, a top view of elliptical intra-annular mounting frame 10 is shown. Once again elliptical intra-annular mounting frame 10 includes a plurality of curvatures 12, interconnecting points 14, and posts 16. As shown in FIG. 3, the base of elliptical intra-annular mounting frame 10 generally defines an ellipse, with a major axis denoted by "D" and a minor axis denoted by "A". In the embodiment of the elliptical intra-annular mounting frame 10 shown in FIG. 3, the ratio of the major axis to the minor axis of the ellipse is about 1.5:1, although in other embodiments of the elliptical intra-annular mounting frame (not shown) the ratio of the major axis to the minor axis of the ellipse can vary generally between about 1.7:1 or 1.8:1 and about 1.1:1 or 1.2:1. In addition, the circumferential distances (distances around the perimeter of the ellipse) between posts 16 in the embodiment of the elliptical intra-annular mounting frame 10 shown in FIG. 3 are roughly equivalent (symmetric; about 33% of the circumference), although in other embodiments of the elliptical intra-annular mounting frame (see, for example, FIG. 5) the circumferential distances between posts 16 can differ, for example two of the circumferential distances between posts 16 can be roughly equivalent while the third circumferential distance can differ from the other two, or all three circumferential distances can be different from each other, depending on the specific geometry of the aortic valve to be repaired. Thus, asymmetric aortic valve geometries can be repaired using the presently described elliptical intra-annular mounting frame.

Figure 4:
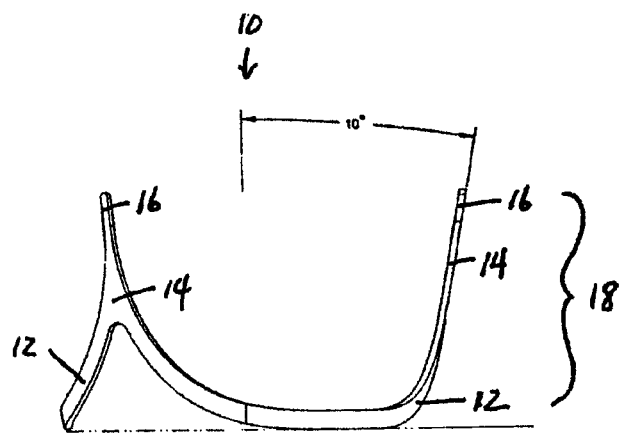
FIG. 4. Side view from "A" (see FIG. 3) of the embodiment of the elliptical intra-annular mounting frame shown in FIG. 1.

Referring now to FIG. 4, a side view of elliptical intra-annular mounting frame 10 is shown. Once again elliptical intra-annular mounting frame 10 includes a plurality of curvatures 12, interconnecting points 14, and posts 16. In the embodiment of the elliptical intra-annular mounting frame 10 shown in FIG. 4, the three edge portions 18 of the elliptical intra-annular mounting frame 10 that comprise interconnecting points 14, posts 16, and upper portions of two curvatures 12 flare outward from the vertical plane of the elliptical intra-annular mounting frame by about 10°. However, in other embodiments of the elliptical intra-annular mounting frame (not shown) the three edge portions 18 can flare outward from the vertical plane of the elliptical intra-annular mounting frame by between about 1° or so and about 30° or so. Although in the embodiment of the elliptical intra-annular mounting frame shown in FIG. 4 the three edge portions 18 each flare outward at equal angles from the vertical plane, in additional embodiments (not shown) the three edge portions 18 can flare outward from the vertical plane at different angles, for example two of the edge portions 18 can flare outward at equal angles from the vertical plane while the third edge portion 18 can flare outward from the vertical plane at a different angle than the other two edge portions 18, or all three edge portions 18 can flare outward at different angles from the vertical plane, depending on the specific geometry of the aortic valve to be repaired.

Different orientations and shapes of the curvatures may be utilized to account for different anatomic variations of the aortic valve. As detailed above in FIG. 1 through FIG. 4, in most embodiments the curvatures are fairly symmetrical to one another, as most aortic valves have 3 cusps of equal sizes. However, in additional embodiments the elliptical intra-annular mounting frame can be produced in an asymmetrical design as some patients have aortic valves with asymmetrical sinuses. Variations could include an elliptical intra-annular mounting frame with one curvature length about 20% larger than the other two curvature lengths, a variation with a single curvature length sized 20% smaller than the other curvature lengths, or variations with each of the curvature lengths having a different size. Additionally, since some patients have an aortic valve that has only two cusps (bicuspid), a bicuspid elliptical intra-annular mounting frame can be produced with two curvatures and two interconnecting points.

Figure 5:
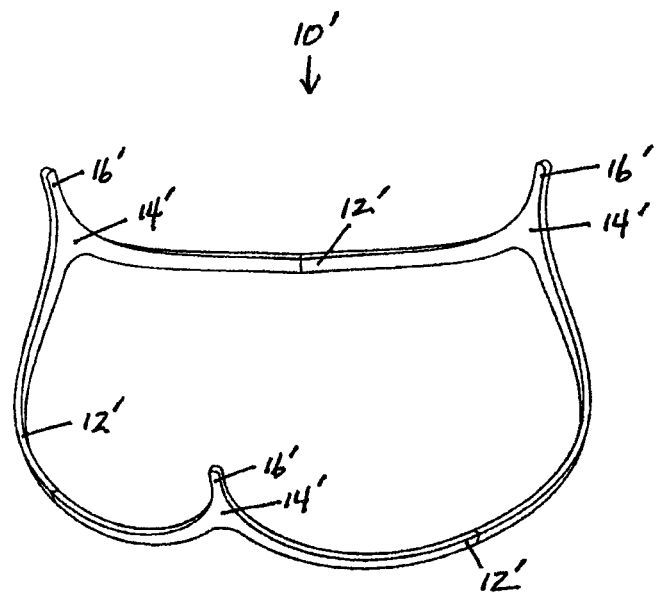
FIG. 5. Perspective view of one embodiment of an asymmetrical elliptical intra-annular mounting frame of the present disclosure.

Referring now to FIG. 5, a perspective view of an embodiment of an asymmetrical elliptical intra-annular mounting frame useful for aortic valve repair is shown and generally designated as numeral 10'. Asymmetrical elliptical intra-annular mounting frame 10' is inserted into the aortic valve annulus and provides for the reconstruction of the native aortic valve having asymmetrical sinuses. Asymmetrical elliptical intra-annular mounting frame 10' includes a plurality of curvatures 12', interconnecting points 14', and posts 16'. As in the case of the symmetrical elliptical intra-annular mounting frame 10 detailed in FIG. 1 through FIG. 4, above, curvatures 12' conform to the annular cusp geometry with interconnecting points 14' and posts 16' conforming to the geometry of the sub-commissural region. Curvatures 12' curve in a plurality of planes of asymmetrical elliptical intra-annular mounting frame 10' to correspond to the three-dimensional geometry of the cusps of an asymmetric aortic valve. For reference, the horizontal plane is defined as the plane on which asymmetrical elliptical intra-annular mounting frame 10' would rest with each curvature 12' contacting the plane. The vertical plane is defined as the plane which intersects the horizontal plane at a perpendicular angle and runs vertically through asymmetrical elliptical intra-annular mounting frame 10'. Curvatures 12' may curve in both the horizontal and vertical planes, and/or may curve in one or more other planes. Generally curvatures 12' contact the aortic wall and provide support and alignment to the aortic valve cusps. Interconnecting points 14' and posts 16' provide support to the commissures of the aortic valve. Specifically, interconnecting points 14' and posts 16' are designed to closely fit the three-dimensional geometry between adjacent cusps and locate near the commissures thus providing support and assistance in the restoration of the proper coaptation of the cusps. Interconnecting points 14' continuously narrow to posts 16' and thus fit within the narrowing space between adjacent cusps that culminates in a commissure. As such, interconnecting points 14' and posts 16' provide support within this inter-cusp space to immediately below the commissures.

Figure 6:
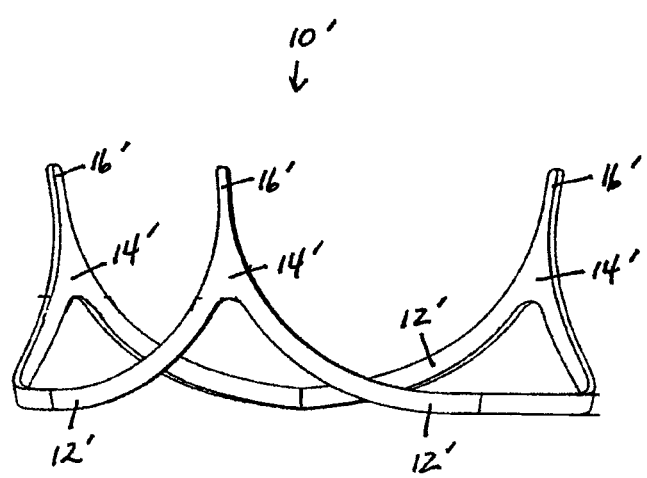
FIG. 6. Front elevational view of the embodiment of the asymmetrical elliptical intra-annular mounting frame shown in FIG. 5.

Referring now to FIG. 6, a front elevational view of asymmetrical elliptical intra-annular mounting frame 10' of FIG. 5 is shown. Once again asymmetrical elliptical intra-annular mounting frame 10' includes a plurality of curvatures 12', interconnecting points 14', and posts 16'.

Figure 7:
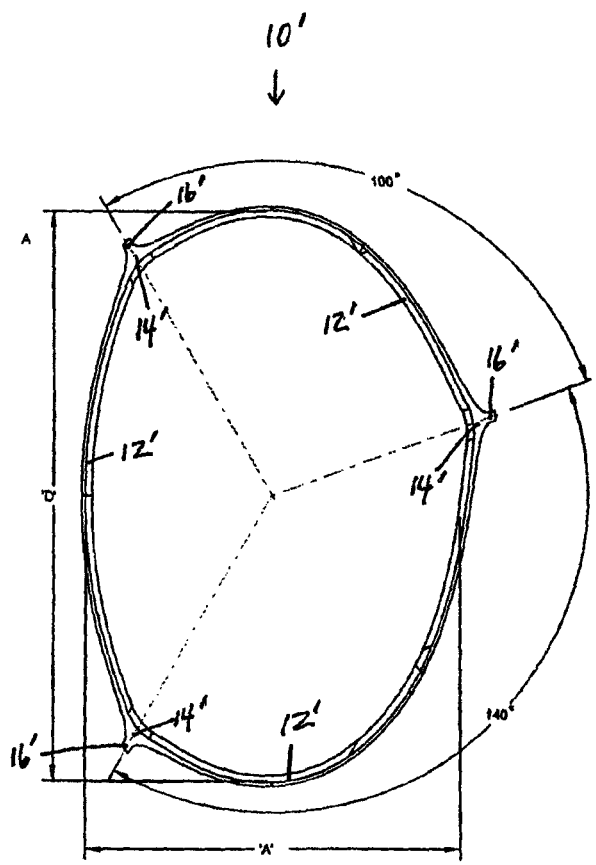
FIG. 7. Top view of the embodiment of the asymmetrical elliptical intra-annular mounting frame shown in FIG. 1.

Referring now to FIG. 7, a top view of asymmetrical elliptical intra-annular mounting frame 10' is shown. Once again asymmetrical elliptical intra-annular mounting frame 10' includes a plurality of curvatures 12', interconnecting points 14', and posts 16'. As shown in FIG. 7, the base of asymmetrical elliptical intra-annular mounting frame 10' generally defines an ellipse, with a major axis denoted by "D" and a minor axis denoted by "A". In the embodiment of the asymmetrical elliptical intra-annular mounting frame 10' shown in FIG. 7, the ratio of the major axis to the minor axis of the ellipse is about 1.5:1, although in other embodiments the asymmetrical elliptical intra-annular mounting frame (not shown) the ratio of the major axis to the minor axis of the ellipse can vary generally between about 1.7:1 or 1.8:1 and about 1.1:1 or 1.2:1. In addition, the circumferential distances (distances around the perimeter of the ellipse) between posts 16' in the embodiment of the asymmetrical elliptical intra-annular mounting frame 10' shown in FIG. 7 are each different (roughly 28%, 33% and 39% of the circumference or perimeter), although in other embodiments of the asymmetrical elliptical intra-annular mounting frame (not shown) two of the circumferential distances between posts 16' can be roughly equivalent while the third circumferential distance can differ from the other two, depending on the specific geometry of the asymmetric aortic valve to be repaired. Thus, all asymmetric aortic valve geometries can be repaired using the presently described asymmetrical elliptical intra-annular mounting frame.

Figure 8:
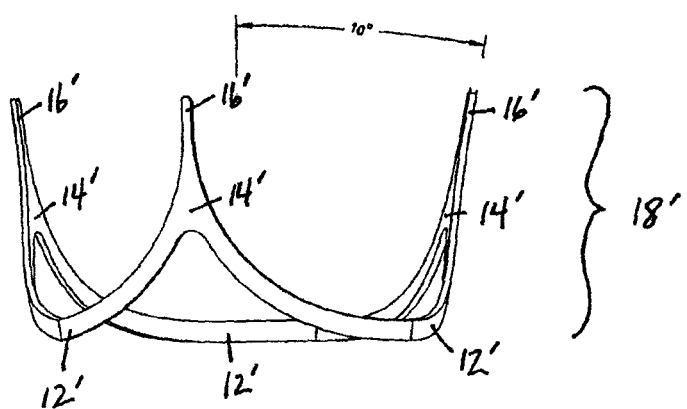
FIG. 8. Side view from "A" (see FIG. 7) of the embodiment of the asymmetrical elliptical intra-annular mounting frame shown in FIG. 1.

Referring now to FIG. 8, a side view of asymmetrical elliptical intra-annular mounting frame 10' is shown. Once again asymmetrical elliptical intra-annular mounting frame 10' includes a plurality of curvatures 12', interconnecting points 14', and posts 16'. In the embodiment of the asymmetrical elliptical intra-annular mounting frame 10' shown in FIG. 8, the three edge portions 18' of the asymmetrical elliptical intra-annular mounting frame 10' that comprise interconnecting points 14', posts 16', and upper portions of the curvatures 12' flare outward from the vertical plane of the asymmetrical elliptical intra-annular mounting frame 10' by about 10°. However, in other embodiments of the asymmetrical elliptical intra-annular mounting frame (not shown) the three edge portions 18' can flare outward from the vertical plane of the asymmetrical elliptical intra-annular mounting frame by between about 1° or so and about 30° or so. Although in the embodiment of the asymmetrical elliptical intra-annular mounting frame 10' shown in FIG. 8 the three edge portions 18' each flare outward at equal angles from the vertical plane (about 10°), in additional embodiments (not shown) the three edge portions 18' can flare outward from the vertical plane at different angles, for example two of the edge portions 18' can flare outward at equal angles from the vertical plane while the third edge portion 18' can flare outward from the vertical plane at a different angle than the other two edge portions 18', or all three edge portions 18' can flare outward at different angles from the vertical plane, depending on the specific geometry of the asymmetric aortic valve to be repaired.

Figure 9:
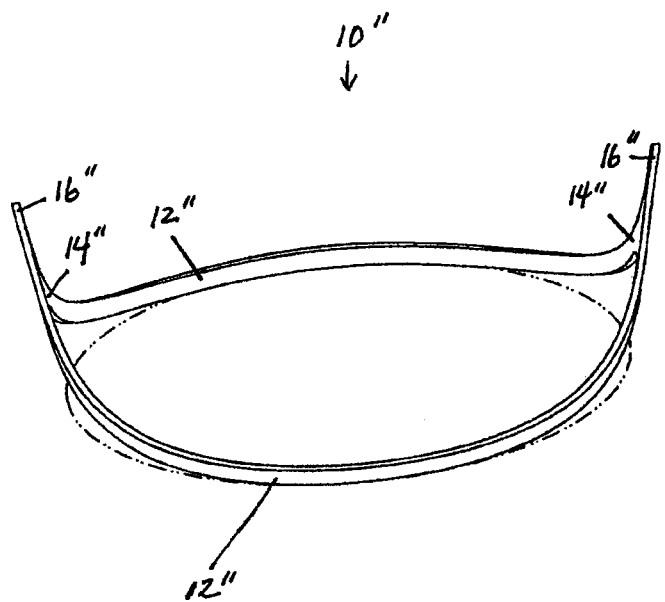
FIG. 9. Perspective view of one embodiment of a bicuspid elliptical intra-annular mounting frame of the present disclosure.

Referring now to FIG. 9, a perspective view of an embodiment of a bicuspid elliptical intra-annular mounting frame useful for bicuspid aortic valve repair is shown and generally designated as numeral 10". Bicuspid elliptical intra-annular mounting frame 10" is inserted into the aortic valve annulus and provides for the reconstruction of the native aortic valve having only two sinuses. Bicuspid elliptical intra-annular mounting frame 10" includes two curvatures 12", interconnecting points 14", and posts 16". As in the case of the symmetrical elliptical intra-annular mounting frame 10 detailed in FIG. 1 through FIG. 4, above, curvatures 12" conform to the annular cusp geometry with interconnecting points 14" and posts 16" conforming to the geometry of the sub-commissural region. Curvatures 12" curve in a plurality of planes of bicuspid elliptical intra-annular mounting frame 10" to correspond to the three-dimensional geometry of the two cusps of a bicuspid aortic valve. For reference, the horizontal plane is defined as the plane on which bicuspid elliptical intra-annular mounting frame 10" would rest with each curvature 12" contacting the plane. The vertical plane is defined as the plane which intersects the horizontal plane at a perpendicular angle and runs vertically through bicuspid elliptical intra-annular mounting frame 10". Curvatures 12" may curve in both the horizontal and vertical planes, and/or may curve in one or more other planes. Generally curvatures 12" contact the aortic wall and provide support and alignment to the aortic valve cusps. Interconnecting points 14" and posts 16" provide support to the commissures of the aortic valve. Specifically, interconnecting points 14" and posts 16" are designed to closely fit the three-dimensional geometry between adjacent cusps and locate near the commissures thus providing support and assistance in the restoration of the proper coaptation of the cusps. Interconnecting points 14" continuously narrow to posts 16" and thus fit within the narrowing space between adjacent cusps that culminates in a commissure. As such, interconnecting points 14" and posts 16" provide support within this inter-cusp space to immediately below the commissures.

Figure 10:
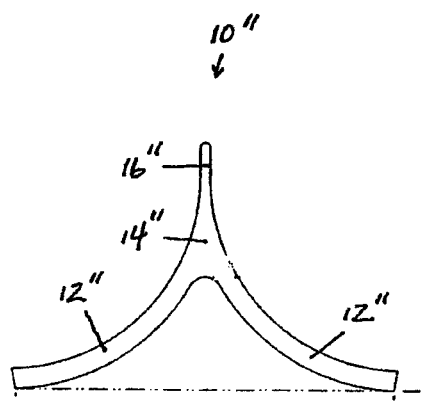
FIG. 10. Front elevational view of the embodiment of the bicuspid elliptical intra-annular mounting frame shown in FIG. 9.

Referring now to FIG. 10, a front elevational view of bicuspid elliptical intra-annular mounting frame 10" is shown. Bicuspid elliptical intra-annular mounting frame 10" includes two curvatures 12", interconnecting points 14", and posts 16".

Figure 11:
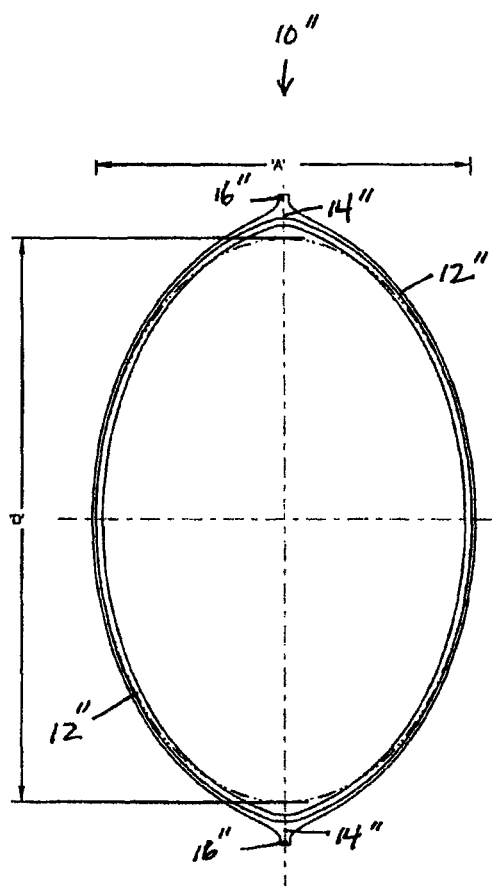
FIG. 11. Top view of the embodiment of the bicuspid elliptical intra-annular mounting frame shown in FIG. 9.

Referring now to FIG. 11, a top view of bicuspid elliptical intra-annular mounting frame 10" is shown. Once again bicuspid elliptical intra-annular mounting frame 10" includes two curvatures 12", interconnecting points 14", and posts 16". As shown in FIG. 11, the base of bicuspid elliptical intra-annular mounting frame 10" generally defines an ellipse, with a major axis denoted by "D" and a minor axis denoted by "A". In the embodiment of the bicuspid elliptical intra-annular mounting frame 10" shown in FIG. 11, the ratio of the major axis to the minor axis of the ellipse is about 1.5:1, although in other embodiments of the bicuspid elliptical intra-annular mounting frame (not shown) the ratio of the major axis to the minor axis of the ellipse can vary generally between about 1.7:1 or 1.8:1 and about 1.1:1 or 1.2:1. In addition, the circumferential distances (distances around the perimeter of the ellipse) between posts 16" in the embodiment of the bicuspid elliptical intra-annular mounting frame 10" shown in FIG. 11 are roughly equivalent (symmetric; about 50% of the circumference), although in other embodiments of the bicuspid elliptical intra-annular mounting frame (not shown) the circumferential distances between posts 16" can differ, for example one circumferential distance of about 75% of the circumference and the other circumferential distance of about 25% of the circumference, one circumferential distance of about 70% of the circumference and the other circumferential distance of about 30% of the circumference, one circumferential distance of about 65% of the circumference and the other circumferential distance of about 35% of the circumference, one circumferential distance of about 60% of the circumference and the other circumferential distance of about 40% of the circumference, one circumferential distance of about 55% of the circumference and the other circumferential distance of about 45% of the circumference, or the like, depending on the specific geometry of the bicuspid aortic valve to be repaired. Thus, all asymmetric bicuspid aortic valve geometries can be repaired using the presently described asymmetrical bicuspid elliptical intra-annular mounting frame.

Figure 12:
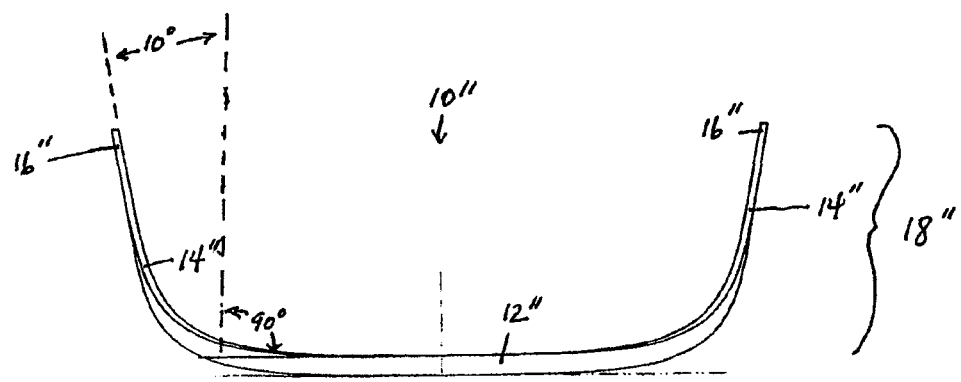
FIG. 12. Side view from "D" (see FIG. 11) of the embodiment of the bicuspid elliptical intra-annular mounting frame shown in FIG. 9.

Referring now to FIG. 12, a side view of bicuspid elliptical intra-annular mounting frame 10" is shown. Once again bicuspid elliptical intra-annular mounting frame 10" includes two curvatures 12", interconnecting points 14", and posts 16". In the embodiment of the bicuspid elliptical intra-annular mounting frame 10" shown in FIG. 12, the two edge portions 18" of the bicuspid elliptical intra-annular mounting frame 10" that comprise interconnecting points 14", posts 16", and upper portions of the two curvatures 12" flare outward from the vertical plane of the bicuspid elliptical intra-annular mounting frame by about 10°. However, in other embodiments of the bicuspid elliptical intra-annular mounting frame (not shown) the two edge portions 18" can flare outward from the vertical plane of the bicuspid elliptical intra-annular mounting frame by between about 1° or so and about 30° or so. Although in the embodiment of the bicuspid elliptical intra-annular mounting frame 10" shown in FIG. 12 the two edge portions 18" each flare outward at equal angles from the vertical plane, in additional embodiments (not shown) the two edge portions 18" can flare outward from the vertical plane at different angles, depending on the specific geometry of the bicuspid aortic valve to be repaired.

Most generally, the major axis of the elliptical intra-annular mounting frame is from about 10 millimeters to about 35 millimeters or so in length, and the minor axis of the elliptical intra-annular mounting frame is from about 8 millimeters to about 25 millimeters or so in length, with a variety of different sized frames there between, forming a gradient of possible choices to closely approximate the needs of the patient. However, larger sizes of the elliptical intra-annular mounting frame can be produced to be utilized with patients that have aortic root aneurysms or Marfan's syndrome. Furthermore, the elliptical intra-annular mounting frame height as measured from the base of a curvature to the tip of a post may vary, but generally ranges from about 8 millimeters to about 15 millimeters or so.

The elliptical intra-annular mounting frame can be comprised of metal, plastics, thermoplastics, polymers, resins or other materials that will remain intact in spite of potentially high tension caused from a highly dilated aortic root. The elliptical intra-annular mounting frame may be constructed of a solid metal wire, solid plastic, or a perforated strip of metal or plastic so as to provide the sutures better purchase once implanted into the aortic valve. The perforations may vary depending on the installation method, though with the generally uniform geometry of the annular region, a set number and position of perforations for sutures may be created and marked onto the elliptical intra-annular mounting frame. In certain embodiments the elliptical intra-annular mounting frame can include a GORE-TEX® coating. In further embodiments, the elliptical intra-annular mounting frame can be covered or coated with a variety of polymers or polymer resins, including, but not limited to, polyethylene terephthalate, sold under the name DACRON® cloth. Alternatively, the elliptical intra-annular mounting frame can be covered with gluteraldehyde-fixed bovine pericardium, which can be useful in certain embodiments as high blood velocities in the outflow tract of the left ventricle could possibly predispose the patient to hemolysis with a cloth covering.

One of the many advantages of the elliptical intra-annular mounting frame is the ease in which the required frame size can be determined preoperatively. Imaging techniques such as Magnetic Resonance Imaging (MRI), echocardiography, or computer tomography (CT)-angiography can be used non-invasively to determine the measurements required to prepare an elliptical intra-annular mounting frame for the patient. In further embodiments the imaging device, including an MRI machine or CT-angiography machine and related controls, could include system parameters and mathematical models and descriptions of the elliptical intra-annular mounting frame that automatically takes the measurements of the patient's aortic valve and outputs the appropriately sized elliptical intra-annular mounting frame required to restore competency of the patient's aortic valve. Additional data output could include the display of various sized intra-annular mounting frames for restoring competency and the effect each different frame would create upon implantation.

In certain embodiments, the presently described elliptical intra-annular mounting frames may have perforations on the curvatures and posts for the passage of sutures therethrough. For example, the sutures may be horizontal mattress sutures, which may then pass into the aortic wall beneath the aortic valve annulus. In one particular arrangement, the sutures could pass deep into the aortic wall, under the cusps, allowing for the insertion of an elliptical intra-annular mounting frame directly into an aortic valve annulus, which would closely correspond to the cusps and commissures. Optionally, three horizontal mattress sutures may be utilized per cusp and one per commissure with a total of twelve sutures used to implant the elliptical intra-annular mounting frame. One of skill in the art would understand that less or more sutures, as well as other attachment techniques known in the art, may be utilized to position and attach the elliptical intra-annular mounting frame into the aortic valve annulus. Above the aortic valve, pledgets may be placed onto the mattress sutures to preclude the possible tearing of aortic tissue. The pledgets may be TEFLON® felt pledgets, or in other embodiments pieces or strips of fabric such as DACRON® may be utilized with the mattress sutures rather than pledgets. The pledgets would generally be small so they would not interfere with the mobility of the aortic valve leaflets.

In an alternative embodiment for installing an elliptical intra-annular mounting frame, support arcs may be employed above the valve annulus, into which sutures could be inserted. Such support arcs may comprise three curvatures with a shape that is substantially similar to those of the elliptical intra-annular mounting frame, which corresponds to the curvature and geometry of the attachment of the cusps to the aortic wall as well as the commissures, resulting in the annulus of the aortic valve being "sandwiched" between the elliptical intra-annular mounting frame and support arcs. Sutures may extend through perforations in the elliptical intra-annular mounting frame through the aortic wall to the support arcs above the cusps, attaching also through perforations in the support arcs. In additional embodiments, the sutures may extend around the support arcs or attach using other methods known in the art.

The described elliptical intra-annular mounting frame and related methods of sizing and implanting the elliptical intra-annular mounting frame could also be applied to other pathologies. With aortic root aneurysms, the elliptical intra-annular mounting frame could allow leaflet-sparing root replacement to be performed from inside the aorta, without the need for extensive external dissection, as with current procedures. A non-porous DACRON® graft may be utilized with the elliptical intra-annular mounting frame after being scalloped and flared in the graft's proximal aspect, to conform to the sinuses of Valsalva. The size of the graft may be selected to match the size of the elliptical intra-annular mounting frame, with consideration also being given for the diameter of the distal aorta. The coronary arteries could then be anastomosed to the side of the graft, either as buttons or with the inclusion technique. Using this simple method, the aortic valve annulus would be fixed in size and geometry, the native aortic valve would be repaired and preserved, and the entire root and ascending aorta could be replaced for root aneurismal disease, with much less dissection and difficulty than with current techniques.

Other pathologies also could be addressed using the described elliptical intra-annular mounting frame. Ultrasonic debridement could be used adjunctively to remove spicules of calcium, and portions of leaflets could be resected and replaced with gluteraldehyde-fixed autologous pericardium. This concept also includes the option of aortic valve single or multiple cusp replacement. With a method of fixing root geometry through reorientation, and potentially undersizing it slightly, more complex repairs could be undertaken, with the elliptical intra-annular mounting frame compensating for slight imperfections. If one cusp were severely diseased or prolapsing, for example, the cusp could be replaced with a gluteraldehyde-fixed autologous (or in certain instances bovine) pericardial cusp (of the appropriate size and geometry to match the size of the elliptical intra-annular mounting frame and native cusps). The artificial cusp could be attached to the arc above the elliptical intra-annular mounting frame, with the elliptical intra-annular mounting frame acting as an attachment for the arc and artificial leaflet. The patient's other valve tissue could be spared, and an entirely competent valve achieved, which then would be two-thirds native tissue. The pericardial leaflet tissue could be treated with contemporary techniques for preventing calcification, but if the artificial leaflet became immobile late postoperatively, it still could act as a coaptation baffle for the other leaflets, and possibly not require additional operations, as can occur with total heterograft replacement.

Prosthetic Valves

In certain embodiments, the present disclosure is directed to systems and methods in which an elliptical valve prosthesis is implanted into the patient. In certain aspects the elliptical valve structure can be composed of biological tissue.

Figure 13:
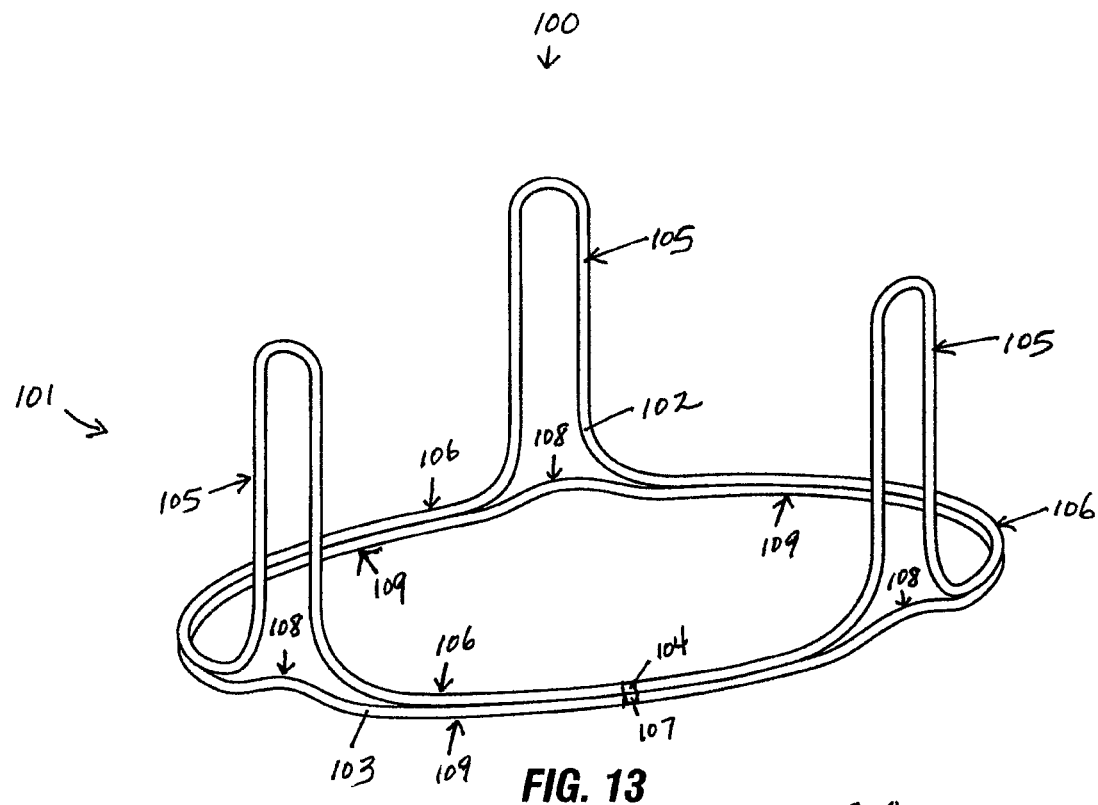
FIG. 13. Perspective view of one embodiment of an elliptical support-valve assembly of the present disclosure.

Referring now to FIG. 13, a perspective view of an embodiment of an elliptical support-valve assembly 100 is shown. In the embodiment of the elliptical support-valve assembly 100 depicted in FIG. 13, the elliptical valve is not shown for purpose of clarity. The elliptical valve (not shown) includes an annulus, leaflets, and commissure points, and in various embodiments can be a mechanical valve, a bileaflet carbon valve, a tissue valve made from a biological material, such as an animal or human valve or tissue, or a synthetic valve, for example made from a polymer. Elliptical support-valve assembly 100 is shown having an elliptical wire frame 101 comprised of elliptical upper wireform 102 and elliptical lower wireform 103. Elliptical upper wireform 102 is a single wire construction formed of flexibly semi-rigid metal, preferably an FDA approved nickel-cobalt alloy such as ELGILOY® having its ends joined at coupling 104 by crimping, welding or other secure coupling process to form an uninterrupted ring having three axially projecting legs 105 to support the commissures of the elliptical valve (not shown). Each leg 105 is joined to an adjacent leg by curved segments 106. Elliptical lower wireform 103 is of similar single wire construction as elliptical upper wireform 102 having its ends joined at coupling 107 in a similar manner to elliptical upper wireform 102 to form an uninterrupted ring having three less pronounced legs 108 beneath the legs 105 of the elliptical upper wireform 102, which are joined by curved segments 109. The elliptical frame 101 of the elliptical support-valve assembly 100 thus defines an elliptical circumferentially repetitive frame.

A flexible biocompatible material (not shown) can be used to cover all surfaces of the elliptical wire frame 101. The flexible biocompatible material is preferably a strong, thin fabric, such as polyester, which separates the core structure of the elliptical wire frame 101 from contact with bodily tissues and blood, and provides a sheath for suturing the elliptical support-valve assembly 100 in place without obstructing the flow of blood through valve (not shown). Alternatively, knitted or bias weave polyesters, PTFE, or woven collagen fibers may all be used to cover the surfaces of the elliptical wire frame 101. The flexible biocompatible material can be configured as an elongated tube closely fitting around the elliptical wire frame 101, or alternatively can be configured as a sheet that includes a pair of longitudinal edges that are folded inward on themselves and sutured together around the elliptical wire frame 101.

Another exemplary elliptical bioprosthetic heart valve assembly generally comprises a full root, stentless elliptical heart valve that is prepared from rectangularly-shaped portions of human or non-human animal heart valve tissue. Preferably, the non-human animal tissue is porcine or bovine tissue. The portions are elongate strips of the original valve that includes intact leaflet material. These portions may be trimmed to remove extraneous muscle tissue. The void resultant from muscle trimming can be filled by the adjacent leaflet. These sections may be subjected to a photochemical fixation procedure, such as described in U.S. Pat. No. 5,147,514, incorporated herein by reference. Alternatively, gluteraldehyde fixation may also be used. In addition, the full root heart valve that has been excised from an animal can be treated either before or after the section with a leaflet has been cut away. If the full heart valve is treated prior to being cut, then the sections may be reassembled with any leaflet section, which provides the desired matching of leaflets.

The elliptical tri-composite bioprosthetic heart valve is formed from three pieces of pre-treated leaflet sections, which have been combined through use of sutures. The valve, which has a generally elliptical shape, includes an external surface and an inner surface. In use, the blood flows through the valve from the inflow end toward the outflow end. The three sections that make up the final valve are stitched together on the edges using sutures, which form a suture line. Each group of sutures includes two groups: hidden sutures and locking sutures. The hidden sutures they do not pierce the interior surface of the valve. This construction technique minimizes the possibility of contact with the leaflet. The hidden sutures can be stitched with a thread having a first color using any suitable technique known to the art, and extend from the edge of the inflow end to a point at which the free margin or edge of the leaflet intersects the interior surface of the valve. The locking sutures are so-called because they resist unraveling even when cut, e.g., when trimmed for implantation, and are generally made by tying a square knot every fourth stitch. The locking sutures can be stitched with a thread having a second color different from first color, and extend from the edge of the outflow end to where the hidden sutures end. The locking sutures serve an important purpose, because they will not unravel when cut by the surgeon while trimming the full root during implantation. Because it can be stitched in a color, preferably a distinct one, different from that of the hidden sutures, it demarks the area of the valve sections that may be trimmed during implantation. Thus, the locking sutures function as trimming guide.

The outside edges of the partially formed valve are then stitched with sutures to form an elongate elliptical body. Each section may include a pericardial tissue covering on the inflow portion. The pericardial covering, which may be stitched into place using known techniques, may serve as a sewing ring. The pericardial covering can be stitched using a blanket stitch such that the individual sutures do not pierce the interior surface of the pericardial covering. The blanket stitch may also serve as a suturing guide for the surgeon. The fully assembled valve may include a sinus in each section of the tri-composite valve. Pericardial extensions can be included on the inflow end and the outflow end of the valve, which can be trimmed by the surgeon to facilitate valve implantation. The extensions may be constructed using locked and hidden sutures as discussed above. The leaflets include cusps that come together in the assembled valve at adjacent edges to form coaptation zones. The leaflet sections may be pre-selected to match the leaflets and limit any gaps in the commissures to thereby optimize operation of the leaflets during use. The size of the heart valve may be varied. In general, the heart valve will have an outside diameter of from about 17 to about 33 millimeters. The size of the valve is typically based on the size of the leaflet sections procured from the donor animal. The size selected for implantation will depend on the requirements of the patient. The heart valves that are excised from the donor animals should preferably be free of anatomical abnormalities and be free of holes in the leaflets or cusps. The leaflet sections may be removed from the donor animals, and the sections cut from the removed animal heart valves, using known techniques.

A further exemplary elliptical prosthetic heart valve assembly generally comprises an elliptical fixation ring in the form of an elliptical suture ring, an elliptical mounting ring, an elliptical retaining ring and an elliptical prosthetic heart valve. The elliptical suture ring and the elliptical mounting ring together form an artificial annulus. The elliptical suture ring can be of any construction that will enable it to be securely affixed to a natural annulus or adjacent body tissue. For example, it may comprise a relatively soft plastic core covered with a suitable cloth, such as a DACRON® cloth. The elliptical suture ring has an outer periphery and an inner periphery that define an opening through the elliptical suture ring.

The elliptical mounting ring is a thin, essentially rigid, elliptical member of metal, such as a biocompatible stainless steel, or suitable plastic material. The elliptical mounting ring has an inner peripheral surface defining an opening through the mounting ring. The elliptical mounting ring can be coupled to the elliptical suture ring in various different ways and in different locations so long as the openings are in appropriate registry so that the prosthetic valve can be received in the opening. In one embodiment, the elliptical mounting ring is mounted in the opening. In this regard, the elliptical mounting ring has an outer peripheral surface that is concave as viewed in axial section and that conforms to the inner periphery of the elliptical suture ring. The elliptical suture ring can be coupled to the elliptical mounting ring and retained thereon by threads of the elliptical suture ring wound around the elliptical mounting ring or in any other suitable manner. The peripheral surface in this embodiment is essentially elliptical. However, a shoulder is formed near the upper end of the elliptical mounting ring, and screw threads lead to the shoulder.

The elliptical retaining ring has external screw threads that cooperate with the threads of the elliptical mounting ring to permit the elliptical retaining ring to be screwed into the upper end of the elliptical mounting ring. Although various constructions are possible, the elliptical retaining ring can project radially inwardly for a short distance into the opening. The elliptical retaining ring is rigid and is constructed of a biocompatible metal or plastic and has a large central opening. Sockets are provided in the upper surface of the elliptical retaining ring to facilitate turning of the elliptical retaining ring into the threads of the elliptical mounting ring.

The elliptical valve may be of essentially conventional construction, except that it includes a relatively rigid elliptical base having a peripheral flange or shoulder. The base may be made rigid by a suitable metal or plastic frame member covered by a suitable fabric. The valve also includes three commissures and three valve leaflets of biological tissue or other suitable material.

In use, the natural heart valve is removed, and the artificial elliptical annulus is sutured to the natural annulus using known surgical techniques, with the peripheral surface of the elliptical mounting ring being essentially flush with the opening defined by the natural annulus. Next, the elliptical valve is inserted into the opening in the desired angular orientation until the flange rests on the shoulder. The elliptical retaining ring is then threadedly attached to the elliptical mounting ring to tightly clamp the flange between the elliptical retaining ring and the shoulder. With this construction, the elliptical retaining ring prevents the elliptical valve from moving upwardly out of the opening, and the flange and the shoulder cooperate to prevent the valve from moving downwardly out of the opening. If it becomes necessary to replace the valve, the elliptical retaining ring is unscrewed from the elliptical mounting ring, and the valve can be lifted upwardly out of the opening. The valve is then replaced with another prosthetic valve, and the new prosthetic valve is retained on the elliptical mounting ring as described above.

Another exemplary elliptical prosthetic valve includes a dimensionally stable, pre-aligned tissue leaflet subassembly, a generally elliptical wireform, and a generally elliptical support stent. The elliptical wireform has a bottom surface dimensioned to receive the pre-aligned tissue leaflet subassembly in fixed, mating engagement. The support stent has an upper surface dimensioned to seat and fix in meeting engagement with the pre-aligned tissue leaflet subassembly, which is fixedly disposed in mating engagement with the bottom surface of the elliptical wireform.

Pursuant to this construction, an exemplary elliptical tissue valve prosthesis includes a plurality of tissue leaflets that are templated and attached together at their tips to form a dimensionally stable and dimensionally consistent coapting leaflet subassembly. Then, in what is essentially a single process, each of the leaflets of the subassembly is aligned with and individually sewn to a cloth-covered elliptical wireform, from the tip of one wireform commissure uniformly, around the leaflet cusp perimeter, to the tip of an adjacent wireform commissure. As a result, the sewed sutures act like similarly aligned staples, all of which equally take the loading force acting along the entire cusp of each of the pre-aligned, coapting leaflets. The resulting elliptical tissue-wireform structural assembly thereby formed reduces stress and potential fatigue at the leaflet suture interface by distributing stress evenly over the entire leaflet cusp from commissure to commissure. This dimensionally stable, reduced-stress assembly is operatively attached to the top of a previously prepared cloth-covered elliptical stent to clamp the tissue leaflet cusps on a load-distributing cloth seat formed by the top of the cloth-covered elliptical stent without distorting the leaflets or disturbing their relative alignment and the resultant coaptation of their mating edges.

The elliptical stent can be secured to the assembly with the commissures of the elliptical stent extending up into the corresponding commissures of the elliptical leaflet, wireform assembly. The elliptical stent itself can be formed of an inner polyester film support secured to a surgically acceptable metal ring such as an ELGILOY® metal stiffener having a cloth cover cut, folded and sewn around the support and stiffener combination. Alternatively, instead of having an ELGILOY® outer band and a laminated polyester film support, the two elliptical stent layers can both be polyester layers or a single piece stent having appropriately flexible commissure posts. Either stent construction provides support and dimensional stability for the valve structure extending from commissure to commissure and being evenly distributed around each leaflet. This assembly methodology allows the evenly sutured tissue of the leaflet cusps to be sandwiched between the elliptical wireform and the stent and to thereby further distribute the loading forces more evenly around the attachment site. Because the tissue leaflets experience lower, more evenly distributed stresses during operation, they are less likely to experience distortion in use. Thus, a more stable, long lived, functional closure or coaptation of the leaflets is provided by this even distribution of attachment forces.

Compressible and Expandable Elliptical Valves

In certain embodiments, the present disclosure is directed to systems and methods in which implanting an elliptical valve prosthesis comprises a compressible and expandable elliptical stent with a collapsible and expandable elliptical valve structure mounted within the stent. In the practice of the embodiment, an insertion catheter is used to advance the elliptical valve prosthesis through a small inlet opening in the chest or groin. The elliptical valve structure can be composed of biological tissue.

The elliptical stent can either be made of a resilient material, such as a self-expandable metal like nitinol (nickel-titanium alloy), or stainless steel, and can be coated with polyethylene or polyurethane. Certain elliptical stents are also expanded by a balloon (for example a nylon elliptical balloon) on the distal end portion of the catheter. When the stent is in place, the balloon is inflated and the stent expands in the body channel such that the outer surface of the stent assumes the final elliptical shape and engages surrounding tissue. In the disclosed devices, the stent is manufactured in an elliptical shape, or is expanded with an elliptical shaped balloon in order to produce the correct fit with the aortic valve.

In certain embodiments an elliptical device includes an elliptical stent that is made from a radially collapsible and re-expandable elliptical support for folding and expanding together with the collapsible elliptical valve. A collapsible elastic elliptical valve made of biological material is typically attached to the stent by gluing, welding or suturing. The metal support can be in the form of a grate, or it can be looped or helical shaped.

Figure 14:
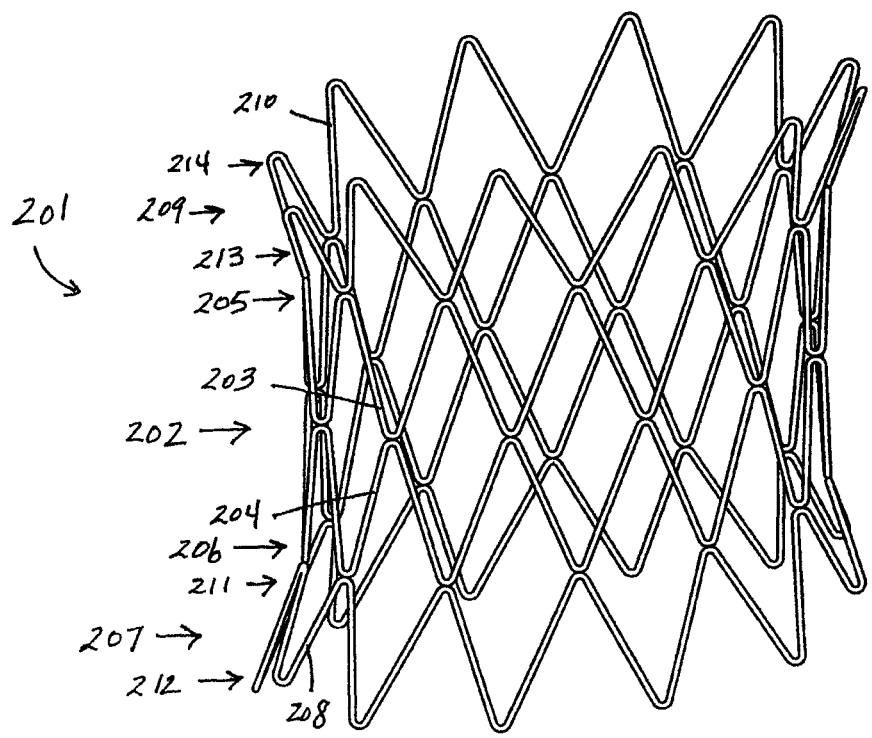
FIG. 14. Perspective view of one embodiment of an alternative elliptical support-valve assembly of the present disclosure.

Referring now to FIG. 14, a perspective view of an embodiment of an elliptical support-valve assembly 200 is shown. In the embodiment of the elliptical support-valve assembly 200 depicted in FIG. 14, the elliptical valve is not shown for purpose of clarity. The elliptical valve includes an annulus, leaflets, and commissure points, and in various embodiments can be a mechanical valve, a bileaflet carbon valve, a tissue valve made from a biological material, such as an animal or human valve or tissue, or a synthetic valve, for example made from a polymer. The expandable elliptical support-valve assembly 200 comprises a tissue valve (not shown) supported on a self-expandable elliptical stent 201 in the form of a wire or a plurality of wires that can be contracted radially in order to make possible the introduction of the elliptical support-valve assembly 200 into the body of the patient by means of a catheter, and that can be deployed in order to allow this structure to engage the wall of the site where the valve is to be deployed. The elliptical valve (not shown) can be supported entirely within a central, self-expandable, elliptical valve support band 202, which in this embodiment is made from a first wire 203 and a second wire 204 configured in a zigzag manner to form the elongate elliptical support band 202 having a first end 205 and a second end 206. In other embodiments (not shown) the elliptical valve support band 202 can be made from a single wire. The elliptical support-valve assembly 200 can also include a proximal anchor 207 and a distal anchor 209, which in this embodiment comprise discrete self-expandable elliptical bands made from single wires 208 and 210, respectively. Proximal elliptical anchor band 207 has a first end 211 connected to the second end 206 of central elliptical valve support band 202 and a second end 212 that is unconnected, and distal elliptical anchor band 209 has a second end 213 that is connected to the first end 205 of the central elliptical valve support band 202 and a first end 214 that is unconnected. This allows the entire elliptical support-valve assembly 200 to expand in unison into place to conform more naturally to the anatomy. The elliptical valve (not shown) is attached to the elliptical valve support band 202 with, for example, one or more sutures. The sutures can be a biologically compatible thread, plastic, metal, or adhesive, such as cyanoacrylate.

The wire can be made from stainless steel, silver, tantalum, gold, titanium, or any suitable tissue or biologically compatible plastic, such as expanded polytetrafluoroethylene or TEFLON®. The central elliptical valve support band 202 may have a series of loops at its ends so that the central elliptical valve support band 202 can be attached to the distal anchor band 209 at its upper end, and the proximal anchor band 207 at its lower end. The link can be made from, for example, stainless steel, silver, tantalum, gold, titanium, any suitable plastic material, or suture.

The elliptical support-valve assembly 200 is compressible about its center axis such that its diameter can be decreased from an expanded position to a compressed position. The elliptical support-valve assembly 200 may be loaded onto a catheter in its compressed position, and so held in place. Once loaded onto the catheter and secured in the compressed position, the elliptical support-valve assembly 200 can be transluminally delivered to a desired location within a body, such as a deficient valve within the heart. Once properly positioned within the body, the catheter can be manipulated to release the elliptical support-valve assembly 200 and expand it into its expanded elliptical shape and position. In one embodiment, the catheter includes adjustment hooks such that the elliptical support-valve assembly may be partially released and expanded within the body and moved or otherwise adjusted to a final desired location. At the final desired location, the elliptical support-valve assembly 200 may be totally released from the catheter and expanded to its full expanded elliptical shape and position. Once the elliptical support-valve assembly 200 is totally released from the catheter and expanded, the catheter may be removed from the body.

Figure 15:
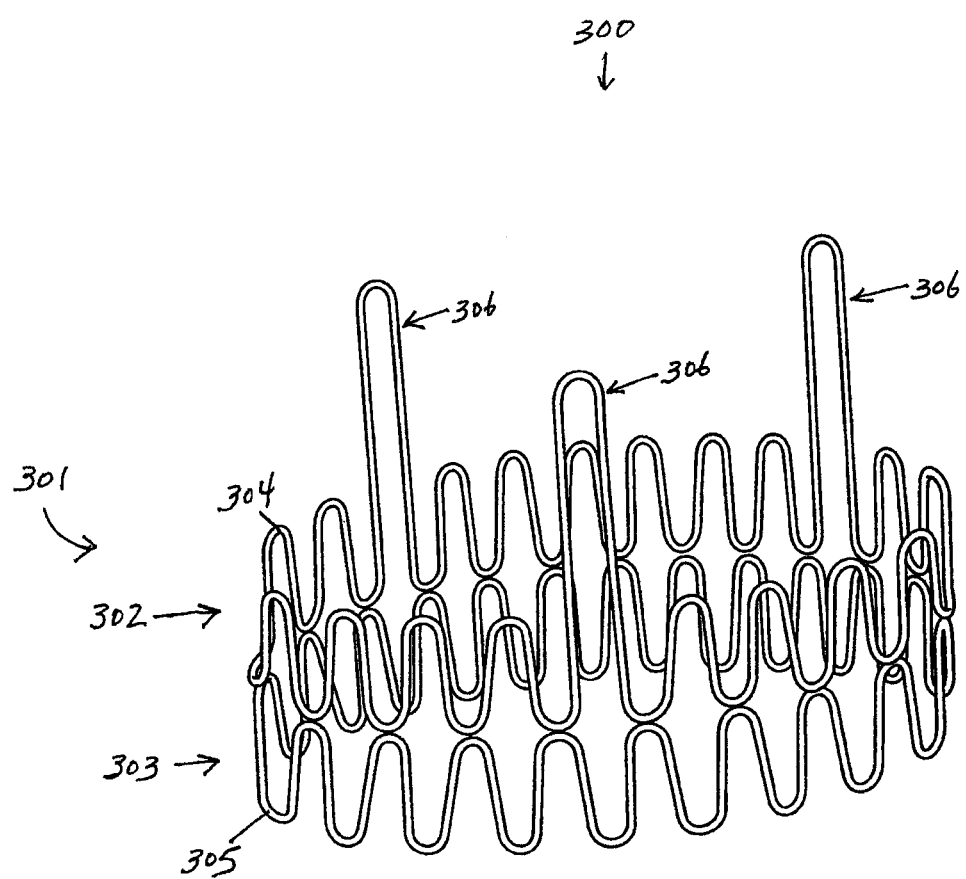
FIG. 15. Perspective view of one embodiment of another alternative elliptical support-valve assembly of the present disclosure.

Referring now to FIG. 15, a perspective view of another embodiment of an elliptical support-valve assembly 300 is shown. In the embodiment of the elliptical support-valve assembly 300 depicted in FIG. 15, the elliptical valve is not shown for purpose of clarity. The elliptical valve includes an annulus, leaflets, and commissure points, and in various embodiments can be a mechanical valve, a bileaflet carbon valve, a tissue valve made from a biological material, such as an animal or human valve or tissue, or a synthetic valve, for example made from a polymer. The elliptical support-valve assembly 300 can be made using an elliptical support means 301 in the form of a first 302 and a second 303 elliptical ring. The first 302 and second 303 elliptical rings are formed using a first 304 and second 305 wires that are folded into loops and bent to form the first 302 and second 303 elliptical rings, which are closed by welding the ends. The first 304 and second 305 wire can be made from stainless steel, silver, tantalum, gold, titanium, or any suitable tissue or biologically compatible plastic, such as expanded polytetrafluoroethylene or TEFLON®. Three of the loops 306 of the first elliptical ring 302 are greater in height than the remaining loops, and are intended to secure the commissural points from an elliptical valve (not shown) that is mounted in the elliptical support means 301. These loops form circumferentially expandable sections between the commissural points forming commissural supports. The first 302 and second 303 elliptical rings are placed on top of each other and are mutually secured, for example using a number of sutures. By using a structure with projecting apices, a reduction in weight is obtained as compared to a stent that is exclusively the same loop heights for all the loops.

In one embodiment, a biological valve (not shown) can be removed from a mammal, such as a pig, and cleaned before mounting in the elliptical support means 301. The cleaned valve has an outer diameter of about 25-27 mm and the height of the three commissural points is about 8 mm. The valve (not shown) is mounted in the elliptical support means 301 by means of a suitable number of sutures to form the elliptical support-valve assembly 300.

The elliptical support-valve assembly 300 is introduced and implanted in the aorta by means of a catheter having an inflatable balloon means. The elliptical support-valve assembly 300 is initially placed above the deflated balloon means and compressed manually around the balloon means. After introduction and positioning, the balloon means is inflated, thereby contributing an elliptical outer dimension to the elliptical support-valve assembly 300. To obtain effective fastening in the aorta, the outer dimension of the elliptical support-valve assembly 300 is greater than the diameter of the aorta. This means that the elliptical support-valve assembly 300 is tight against the inner wall of the aorta with a pressure that is sufficiently large to counteract a detachment due to the flow of the blood. The balloon catheter may subsequently be removed from the aorta. Due to the stiffness of the metal the elliptical support-valve assembly 300 will prevent a contraction. However, smaller contractions may occur (<10% diameter reduction) after the deflation and removal of the balloon catheter.

The elliptical support-valve assembly 300 can be positioned in the aorta in three different positions, i.e., in a position between the coronary arteries and the left ventricle of the heart, in a position immediately after the mouth of the coronary arteries in the ascending part of the aorta, and in a position in the descending part of the aorta, in accordance with the diagnosis of the illness of the patient.

Non-Axisymmetrically Constructed Aortic Devices

In certain embodiments, the present disclosure is directed to systems and methods in which implanting a non-axisymmetric aortic valve device, implant or prosthesis comprises implanting a device that has a generally axisymmetric (e.g., circular) shape but is specifically designed and constructed to adopt a non-axisymmetric shape upon placement in the aortic valve region. In certain aspects one or more portions of the device, implant or prosthesis can be composed of biological tissue.

Figure 16:
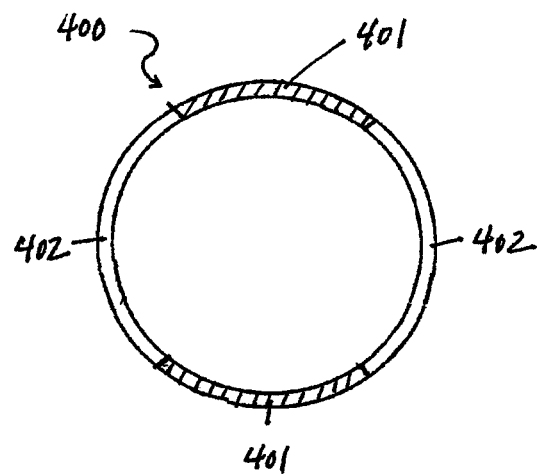
FIG. 16. Top view of one embodiment of a non-axisymmetrically constructed aortic ring of the present disclosure.

Referring now to FIG. 16, a top view of an embodiment of a non-axisymmetrically constructed aortic ring 400 is shown. Although shown as a simple ring for ease of representation, the skilled artisan will realize that the non-axisymmetrically constructed aortic devices, implants or prostheses of the present disclosure can generally resemble any of the devices, implants or prostheses shown herein wherein the initial shape is generally axisymmetric but that adopts a non-axisymmetric shape once in the desired final location due to the non-axisymmetric design and construction. As shown in FIG. 16 the ring 400 comprises four different sections, two of which (401) are comprised of a first material or thickness of material and the other two of which (402) are comprised of a second material or thickness of material. In general sections 401 and 402 have different elastic coefficients such that the ring 400 can adopt a non-axisymmetric shape when placed into the aortic valve region. For example, sections 401 can have a greater resistance to compression than sections 402 such that when ring 400 is compressed sections 402 flatten while sections 401 maintain their original shape, resulting in ring 400 having a generally elliptical (non-axisymmetric) shape. Such non-axisymmetric construction can generally utilize different materials, including, but not limited to, different metals, different alloys, different polymers, or any combination thereof, or different thickness of materials, or a combination of different materials and different thickness of materials.

Figure 17:
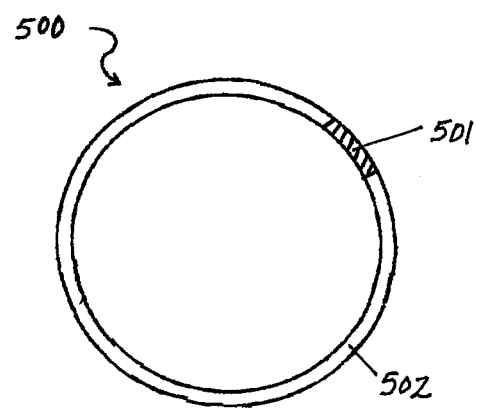
FIG. 17. Top view of an alternative embodiment of a non-axisymmetrically constructed aortic ring of the present disclosure.

Referring now to FIG. 17, a top view of an alternative embodiment of a non-axisymmetrically constructed aortic ring 500 is shown. Although shown as a simple ring for ease of representation, the skilled artisan will realize that the non-axisymmetrically constructed aortic devices, implants or prostheses of the present disclosure can generally resemble any of the devices, implants or prostheses shown herein wherein the initial shape is generally axisymmetric but that adopts a non-axisymmetric shape once in the desired final location due to the non-axisymmetric design and construction. As shown in FIG. 17 the ring 500 comprises two different sections, one of which (501) is comprised of a first material or thickness of material and the other of which (502) is comprised of a second material or thickness of material. In general sections 501 and 502 have different elastic coefficients such that the ring 500 can adopt a non-axisymmetric shape upon placement into the aortic valve region. For example, section 501 can have a lesser resistance to compression than section 502 such that when ring 500 is compressed section 501 flattens while section 502 maintains its original shape, resulting in ring 500 having a non-axisymmetric shape. Such non-axisymmetric construction can generally utilize different materials, including, but not limited to, different metals, different alloys, different polymers, or any combination thereof, or different thickness of materials, or a combination of different materials and different thickness of materials.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

EXAMPLE 1

The inventors obtained and analyzed high resolution multi-slice computer tomography (CT) angiograms of healthy human aortic valves. Using 1 mm axial slices, CT angiograms from 10 normal aortic roots generated x, y, and z coordinates of valve structures in Mathematica. Three-dimensional least squares regression of leaflet and sinus coordinates was employed to compare hemispherical and ellipsoidal models. Shapes and dimensions of all root structures were evaluated.

Normal valve geometry could be represented as three hemispheres nested within a cylinder. However, dimensional fits were better using ellipsoidal geometry, with taller leaflets than predicted by hemispheres. Leaflet/sinus horizontal circumference was fairly circular (average minor-major ratio=0.82-0.87). The base of the valve was quite elliptical (minor-major ratio=0.65), and this geometry extended vertically. The commissure between the left (LC) and non-coronary (NC) cusps was located at the posterior junction of the base minor diameter and circumference, with the center of the right coronary (RC) cusp opposite. Centrums of the LC, NC, and RC leaflet/sinus ellipsoids were migrated toward the center of the valve (average fractional migration or alpha=0.24, 0.32, and 0.09, respectively). The commissures flared outward by 5-10 degrees, and the RC cusp was the largest (Table 1).

TABLE 1

| Structure | Base | NC | RC | LC |
| --- | --- | --- | --- | --- |
| Circumference | 73.7 mm | — | — | — |
| Leaflet Height | — | 12.7 mm | 12.9 mm | 12.5 mm |
| Major Axis | 14.1 mm | 8.6 mm | 9.5 mm | 8.7 mm |
| Minor Axis | 9.1 mm | 7.4 mm | 7.8 mm | 7.6 mm |
| Minor/Major Axis Ratio | 0.65 | 0.86 | 0.82 | 0.87 |
| Alpha | — | 0.32 | 0.09 | 0.24 |
| Leaflet Area | — | 616 mm$^2$ | 670 mm$^2$ | 620 mm$^2$ |
| Leaflet Volume | — | 1959 mm$^3$ | 2238 mm$^3$ | 1998 mm$^3$ |

Furthermore, examination of the sub-commissural regions showed that the commissures flared outward from the center of the valve by about 5 to 10 degrees. Therefore, mounting frames were designed with an elliptical cross-section with narrowed and flared posts, as described herein and below.

EXAMPLE 2

The currently described intra-annular mounting frame with an elliptical cross-section of 1.5 axis ratio (major axis/minor axis, or 0.66 axis ratio minor axis/major axis) and 10° outward post flaring was tested in calves with promising results, as detailed below.

Mounting frames were implanted into 10 calves for survival studies at the Texas Heart Institute. Calves were used as the implant model because calves have valves that are near-human size, providing good correspondence to the devices that will be used clinically in humans. Echocardiography analysis of the repaired valve showed good leaflet coaptation, normal leaflet opening, no leaks, and undisturbed laminar flow. CT-angiography showed normal elliptical leaflet geometry and coaptation during diastole, and good opening of the valve leaflets during systole. These findings were confirmed using root angiography.

At autopsy, endoscopy was performed under water pressurization, and it was shown in all of the calves that the leaflets were nicely aligned with good verticality and no coaptation problems—they meet in the midline, and the pledgets are well-endothelialized.

The presently described elliptical mounting frame is currently scheduled to undergo clinical testing.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A non-axisymmetric device for implantation into a native aortic valve of a mammal comprising a non-axisymmetric cross-sectional shape, a base and commissure support members attached to the base, wherein the members flare outwardly from the base at an angle of from about 1° to about 30° from a line perpendicular to the outer edge of the non-axisymmetric cross-sectional shape.

2. The device of claim 1, wherein the device comprises an elliptical cross-sectional shape.

3. The device of claim 1, wherein the members flare outwardly from the base at an angle of from 8°-12° from a line perpendicular to the outer edge of the non-axisymmetric cross-sectional shape.

4. The device of claim 1, wherein the members extend away from the base at an outward angle of about 10° from a line perpendicular to the outer edge of the elliptical cross-section.

5. The device of claim 1, wherein the non-axisymmetric cross-sectional shape has a major axis and a minor axis, and wherein the ratio of the major axis to the minor axis is between about 1.1 and 1.8.

6. The device of claim 5, wherein the ratio of the major axis to the minor axis is about 1.5.

7. The device of claim 1, wherein the non-axisymmetric cross-sectional shape has a major axis having a length between about 10 millimeters and about 35 millimeters.

8. The device of claim 1, wherein the non-axisymmetric cross-sectional shape has a minor axis having a length between about 8 millimeters and about 25 millimeters.

9. The device of claim 1, wherein the device is non-axisymmetrically constructed.

10. The device of claim 9, wherein the device comprises at least two different materials.

11. The device of claim 9, wherein the device comprises at least two different thicknesses of a material.

12. The device of claim 1, wherein the device comprises a plastic, a polymer, a metal, a thermoplastic, a resin, or combinations thereof.

13. The device of claim 12, wherein the device comprises metal.

14. The device of claim 13, wherein the device comprises metal wire.

15. The device of claim 1, wherein the device comprises animal tissue.

16. The device of claim 1, wherein at least a portion of the device is coated or covered.

17. The device of claim 16, wherein at least a portion of the device is coated or covered with a polymer cloth.

18. The device of claim 1, wherein the device is constructed of a compressible and expandable material effective to be compressible into a percutaneous delivery system and expandable to a non-axisymmetric geometry when released.

19. The device of claim 18, wherein the device is expandable to an elliptical geometry when released.

20. The device of claim 18, wherein the device is self-expanding.

21. The device of claim 20, wherein the device comprises Nitinol.

22. The device of claim 1, wherein the device avoids or reduces pressure on the atrioventricular node when placed into the aortic valve region.

23. The device of claim 1, wherein the device is a non-axisymmetric valve prostheses.

* * * * *